(12) United States Patent
Harris et al.

(10) Patent No.: US 11,300,216 B2
(45) Date of Patent: Apr. 12, 2022

(54) DEVICES, SYSTEMS, AND METHODS FOR MEDICAL CLEANING VALVES

(71) Applicant: Boston Scientific Scimed, Inc., Maple Grove, MN (US)

(72) Inventors: Colby Harris, Weston, MA (US); Larry E. Stanton, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/868,329

(22) Filed: May 6, 2020

(65) Prior Publication Data
US 2020/0355281 A1 Nov. 12, 2020

Related U.S. Application Data

(60) Provisional application No. 63/002,759, filed on Mar. 31, 2020, provisional application No. 62/923,197, (Continued)

(51) Int. Cl.
*F16K 11/07* (2006.01)
*A61B 1/00* (2006.01)
(Continued)

(52) U.S. Cl.
CPC ...... *F16K 11/0712* (2013.01); *A61B 1/00068* (2013.01); *A61B 1/00137* (2013.01);
(Continued)

(58) Field of Classification Search
CPC .. F16K 11/0712; F16K 11/0716; A61B 90/92; A61B 90/94; A61B 90/70;
(Continued)

(56) References Cited

U.S. PATENT DOCUMENTS 4,361,138 A * 11/1982 Kinoshita .......... A61B 1/00068
600/159
4,537,209 A * 8/1985 Sasa ................... A61B 1/00137
134/102.1
(Continued)

FOREIGN PATENT DOCUMENTS

EP    3073889 A1   10/2016
JP    2006056508 A  3/2006
(Continued)

OTHER PUBLICATIONS

International Search Report and Written Opinion for Application No. PCT/US2020/031688, dated Nov. 8, 2020, 12 pages.
(Continued)

*Primary Examiner* — Daphne M Barry
*Assistant Examiner* — Patrick C Williams
(74) *Attorney, Agent, or Firm* — Seager, Tufte & Wickhem LLP.

(57) ABSTRACT

A medical cleaning valve (or cleaning valve) may be configured to provide cleaning functionality to fluid (e.g., air and water) channels of an endoscope. Many embodiments described herein may include a cleaning valve (or valve) that is appropriate for single-use and therefore may be disposable. Accordingly, the valve may be made from a limited number of parts and materials, e.g., to limit its cost and/or manufacturing complexity. For example, multiple seals may be integrally formed with a valve stem. In another example, the valve may have an interface member, which may combine and simplify the functionality of a number of components, such as by connecting the valve stem to a valve well, sealing an opening to a lumen in the valve stem, and/or biasing the valve stem into a position relative to the valve well.

19 Claims, 21 Drawing Sheets

Related U.S. Application Data filed on Oct. 18, 2019, provisional application No. 62/844,465, filed on May 7, 2019.

(51) Int. Cl.

| | | |
|---|---|---|
| *A61B 1/12* | (2006.01) | |
| *A61B 90/92* | (2016.01) | |
| *A61L 2/18* | (2006.01) | |
| *A61M 39/16* | (2006.01) | |
| *A61M 25/00* | (2006.01) | |
| *A61M 39/26* | (2006.01) | |
| *A61B 90/94* | (2016.01) | |
| *A61B 90/70* | (2016.01) | |

(52) U.S. Cl.
CPC ............. *A61B 1/126* (2013.01); *A61B 90/70* (2016.02); *A61B 90/92* (2016.02); *A61B 90/94* (2016.02); *A61L 2/18* (2013.01); *A61M 39/16* (2013.01); *F16K 11/0716* (2013.01); *A61B 1/125* (2013.01); *A61B 2090/701* (2016.02); *A61L 2202/24* (2013.01); *A61M 25/007* (2013.01); *A61M 2039/267* (2013.01); *A61M 2205/583* (2013.01); *A61M 2207/00* (2013.01)

(58) Field of Classification Search
CPC . A61B 1/00068; A61B 1/00137; A61B 1/126; A61B 1/125; A61B 2090/701; A61L 2/18; A61L 2202/24; A61M 39/16; A61M 25/007; A61M 2039/267; A61M 2205/583; A61M 2207/00
See application file for complete search history.

(56) References Cited

U.S. PATENT DOCUMENTS

| | | | |
|---|---|---|---|
| 4,694,821 A * | 9/1987 | Kondo | ................. A61B 1/12 600/158 |
| 5,027,791 A * | 7/1991 | Takahashi | ............. A61B 1/126 600/158 |
| D391,881 S | 3/1998 | Youseph et al. | |
| D453,830 S | 2/2002 | McDowell et al. | |
| 6,346,075 B1 * | 2/2002 | Arai | ................... A61B 1/00068 600/159 |
| D611,599 S | 3/2010 | Eisenkolb et al. | |
| D638,537 S | 5/2011 | Virr et al. | |
| 8,771,223 B2 | 7/2014 | Patton et al. | |
| D749,742 S | 2/2016 | Ishibashi et al. | |
| 9,314,269 B2 | 4/2016 | Webb et al. | |
| D779,636 S | 2/2017 | Gross | |
| D855,795 S | 8/2019 | Ritter, III et al. | |
| D861,161 S | 9/2019 | Schuessler | |
| D862,694 S | 10/2019 | Narnekar et al. | |
| D885,571 S | 5/2020 | Haddad et al. | |
| D923,196 S | 6/2021 | Fang et al. | |
| 2013/0276338 A1 | 10/2013 | Amaral | |
| 2013/0303844 A1 * | 11/2013 | Grudo | ................. A61B 1/0011 600/101 |
| 2015/0144215 A1 * | 5/2015 | Bellofatto | ............ A61B 1/0011 137/625.69 |
| 2017/0143194 A1 | 5/2017 | Wolfe | |
| 2017/0347860 A1 | 12/2017 | Still et al. | |

FOREIGN PATENT DOCUMENTS

| | | |
|---|---|---|
| JP | 2018514448 A | 6/2018 |
| JP | D1136651 S | 6/2018 |
| WO | 03030962 A2 | 4/2003 |
| WO | 2013142211 A1 | 9/2013 |
| WO | 2019226307 A1 | 11/2019 |
| WO | 2020014376 A1 | 1/2020 |

OTHER PUBLICATIONS

International Search Report and Written Opinion for Application No. PCT/US2020/031687, dated Feb. 9, 2020, 13 pages.

* cited by examiner

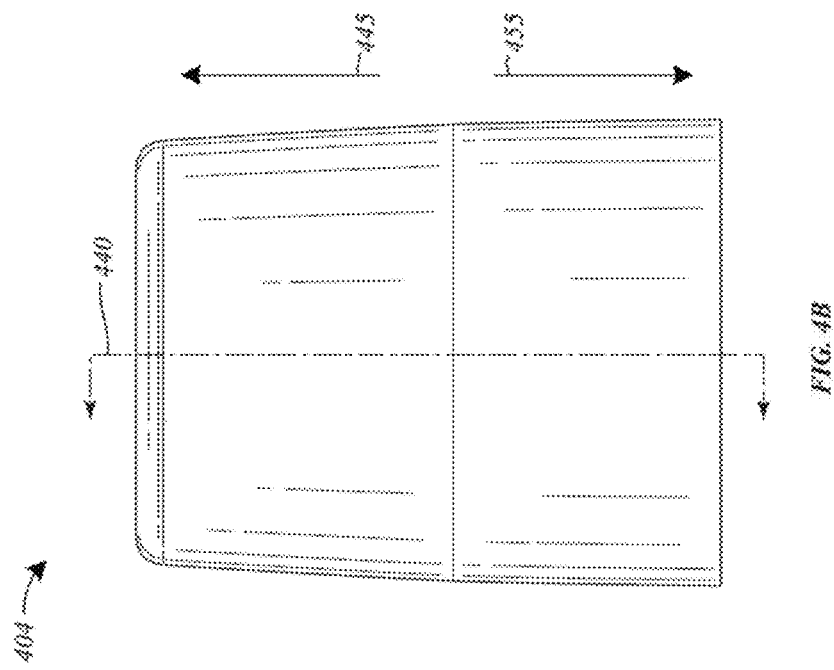
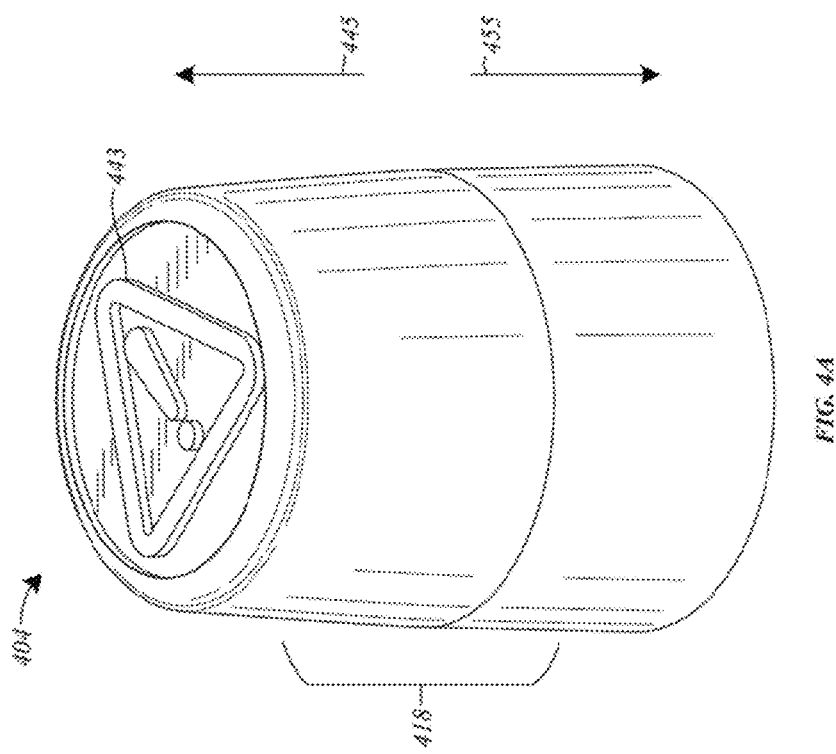

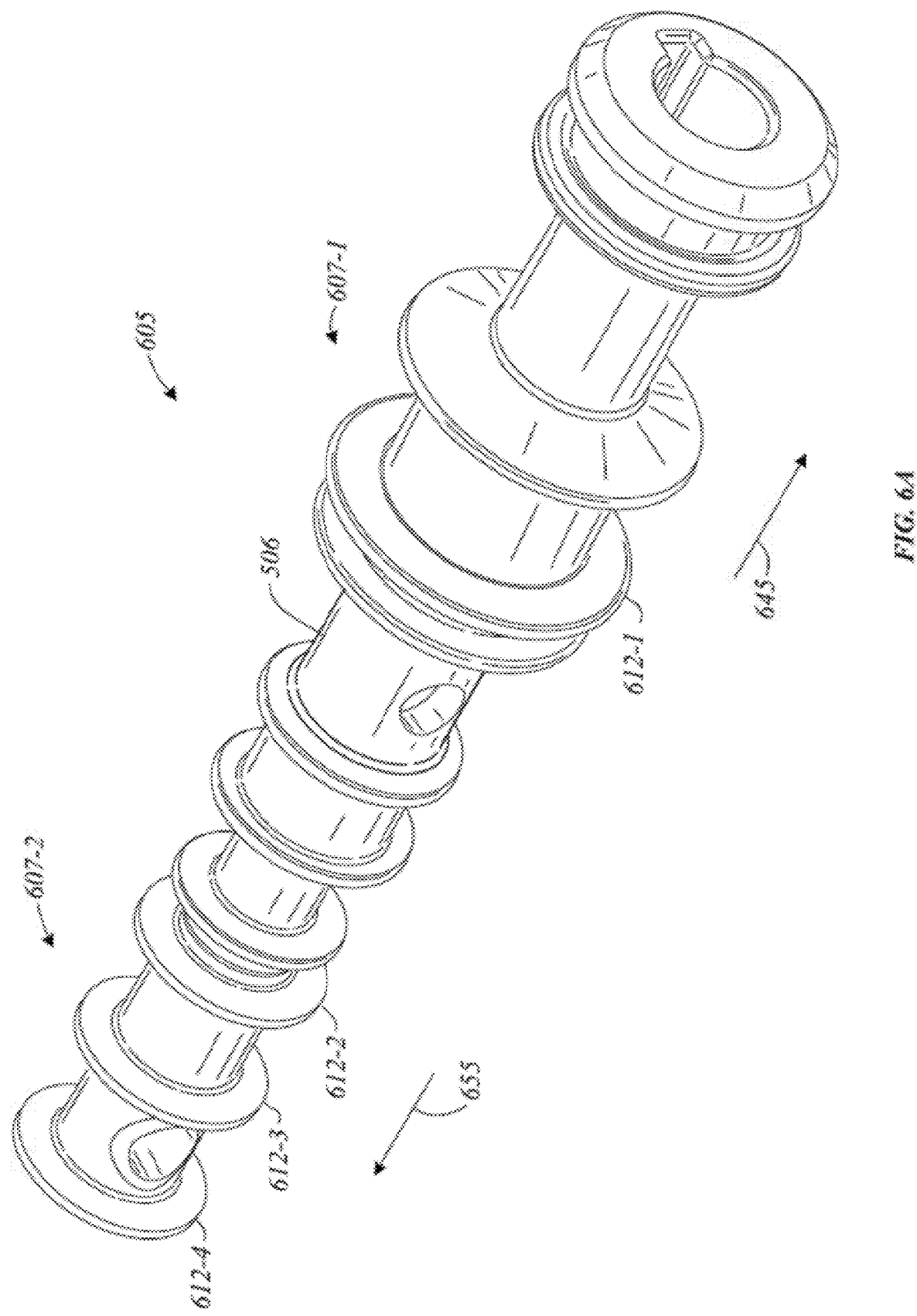

DEVICES, SYSTEMS, AND METHODS FOR MEDICAL CLEANING VALVES

RELATED APPLICATIONS

This application claims the benefit of priority under 35 U.S.C. § 119 to U.S. Provisional Application No. 62/844,465, titled "Medical Cleaning Valve", filed on May 7, 2019, the entirety of which is incorporated herein by reference.

This application claims the benefit of priority under 35 U.S.C. § 119 to U.S. Provisional Patent Application No. 62/923,197, titled "Devices, Systems, Methods, and Designs for Medical Cleaning Valves", filed on Oct. 18, 2019, the entirety of which is incorporated herein by reference.

This application claims the benefit of priority under 35 U.S.C. § 119 to U.S. Provisional Patent Application No. 63/002,759, titled "Devices, Systems, and Methods for Medical Cleaning Valves", filed on Mar. 30, 2020, the entirety of which is incorporated herein by reference.

FIELD

The present disclosure relates generally to valves for medical devices. In particular, the present disclosure relates to cleaning valves for medical devices.

BACKGROUND

Endoscopes include functionality to deliver fluids to (including air and water) and suction at a site of a procedure. Tubing for delivering fluids and/or suction extends from a handle of the endoscope, through a shaft of the endoscope, and to a distal tip of the endoscope. During a procedure, body fluids, tissues, or other material can build up in the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. To accomplish this, a cleaning valve may be inserted into an air/water valve cylinder of an endoscope after the scope is removed from a patient and the procedure valve is removed from the valve cylinder. An operator may then depress a button of the cleaning valve for a predetermined amount of time (e.g., 30 seconds) to flush the air and/or water channels of the endoscope with air and/or the air channel with water prior to further reprocessing of the endoscope. One option for accomplishing such pre-processing is a reusable cleaning valve. Such reusable cleaning valves may include a number of components, including a valve stem (often made of metal), a number of seals, a spring, a spring housing, a boot, and/or an interface member (e.g., stem cap or button). Many components in a reusable cleaning valve may be removable and/or replaceable components, such as to facilitate repairs to be performed on the reusable cleaning valve. However, replaceability of cleaning valve components can increase the cost and complexity of the cleaning valve. For example, manufacturing many separate components and assembling them together can considerably increase both the cost and complexity of a cleaning valve. Further, a reusable cleaning valve must be subject to cleaning, itself, in between uses, which can add to reprocessing cost. It is with all of the above considerations in mind that the improvements of the present disclosure may be useful.

SUMMARY

In one aspect, the present disclosure relates to a valve for a medical device comprising a valve stem and one or more seals. The valve stem may include a proximal end, a distal end, one or more orifices, and a lumen in fluid communication with at least one orifice of the one or more orifices. The one or more seals may be positioned between the proximal and distal ends of the valve stem. The valve stem and the one or more seals may comprise a unitary structure. In many embodiments, the valve stem and the one or more seals may comprise a first material. In many such embodiments, the first material may comprise a polymer. In some embodiments, the proximal end of the valve stem may comprise an orifice of the one or more orifices. In some such embodiments, the valve stem is configured to couple with an interface member. In several embodiments, the valve may include the interface member and the interface member may be configured to seal the orifice when the valve stem is coupled with the interface member. In various embodiments, the interface member may be configured to surround at least one seal of the one or more seals when the valve stem is coupled with the interface member. In some embodiments, one or more orifices may comprise first and second orifices positioned between the proximal and distal ends of the valve stem. In some such embodiments, the one or more seals may comprise first and second seals positioned between the first and second orifices. In further embodiments, the one or more seals may comprise a third seal positioned distal of the first and second orifices. In one or more embodiments, the one or more seals may include a seal with a first portion having a first thickness and a second portion having second thickness thinner than the first thickness. In one or more such embodiments, the first thickness is greater than 0.015 inches and the second thickness is less than 0.015 inches. In further embodiments, the first thickness of the seal transitions into the second thickness of the seal at an angle between 25 and 45 degrees. In some embodiments, the second portion may extend at least 0.01 inches radially outward beyond the first portion. In many such embodiments, the second portion is configured to form an interference fit with a valve well. In one or more embodiments, each seal of the one or more seals may be configured to form an interference fit with a valve well.

In another aspect, the present disclosure relates to a method of manufacture. The method may include forming, as a unitary structure, a valve stem including a proximal end, a distal end, one or more seals, one or more orifices, and a lumen in fluid communication with at least one orifice of the one or more orifices. In various embodiments, the method may include sealing at least one orifice of the one or more orifices with an interface member. In some embodiments, the method may comprise removing a forming core pin from the lumen via an orifice of the one or more orifices, wherein the orifice is comprised in the proximal end of the valve stem. In various embodiments, the method may comprise forming the valve stem with a closed distal end. In one or more embodiments, the method may include forming the valve stem from a polymer material. In several embodiments, the method may comprise forming at least one seal of the one or more seals with a first portion having a first thickness and a second portion having a second thickness, wherein the second portion is radially outward of the first portion and the second thickness is thinner than the first thickness.

In yet another aspect, the present disclosure relates to a valve for a medical device comprising an interface member, a valve stem, and two or more seals. The interface member may be removably couplable to the valve stem. The valve stem may include a proximal end, a distal end, two or more orifices, and a lumen in fluid communication with first and second orifices of the two or more orifices. The first orifice may be located proximate the distal end of the valve stem. The lumen may be plugged at the proximal end of the valve stem by the interface member. The two or more seals may include first and second seals with the first seal positioned between the proximal end of the valve stem and the second orifice and the second seal positioned between the second orifice and the distal end of the valve stem. In many embodiments, the distal end of the valve stem is closed and the lumen terminates at or distally beyond the first orifice and before the closed distal end.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 4A-4C illustrate various aspects of an exemplary interface member according to the present disclosure described herein.

FIGS. 6A-6H illustrate various aspects of an exemplary valve stem assembly according to the present disclosure described herein.

DETAILED DESCRIPTION

Figure 1A:
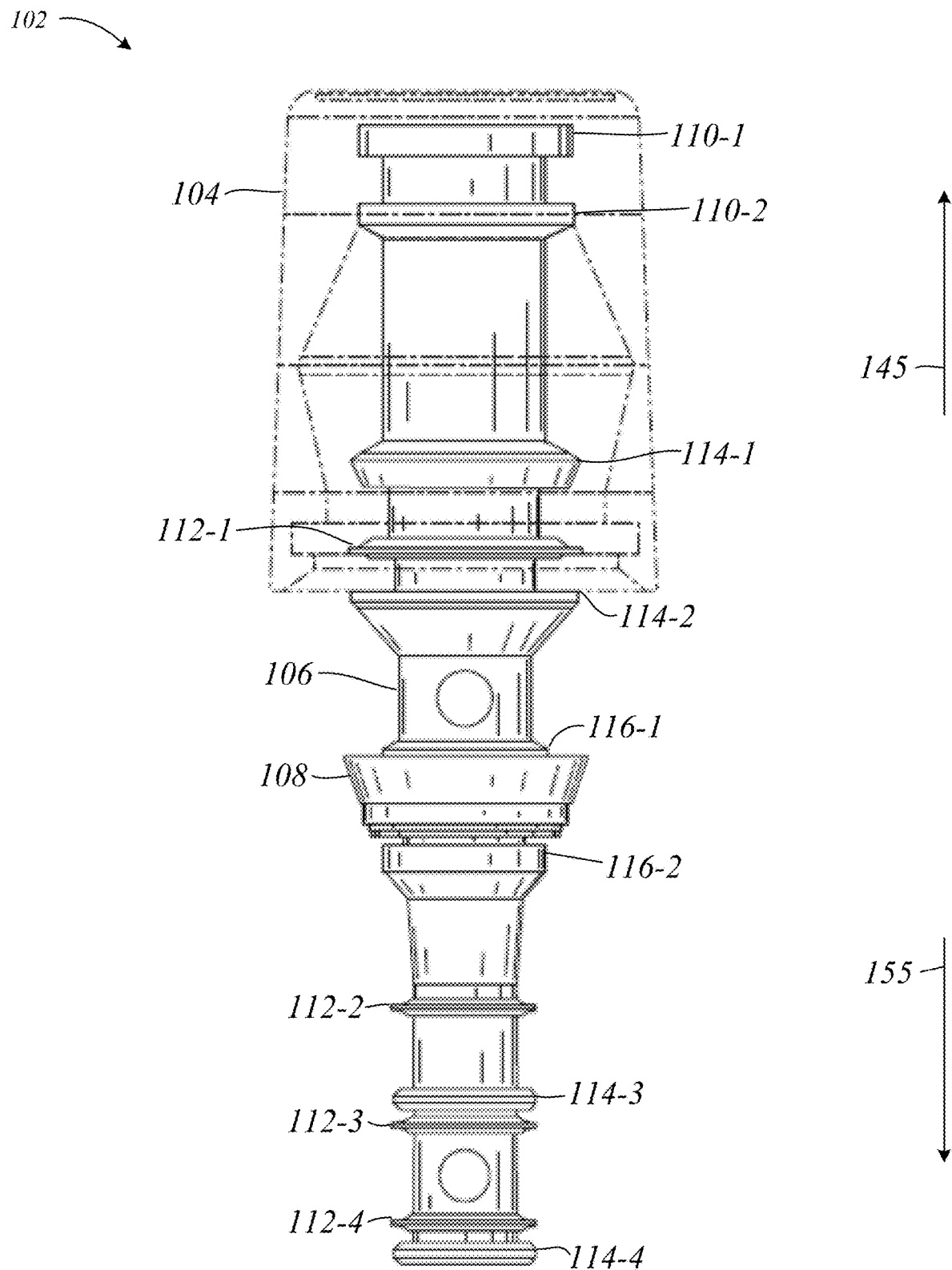
FIG. 1A illustrates a front view of an exemplary cleaning valve according to the present disclosure described herein.

A medical cleaning valve (or cleaning valve) may be configured to provide cleaning functionality to fluid (e.g., air and water) channels of an endoscope. In a first configuration, the cleaning valve may provide a continuous feed of air (or carbon dioxide) to both air and water channels in a handle and shaft of an endoscope, and through an air/water nozzle at the distal end of the endoscope. In a second configuration, the cleaning valve may feed water into the air channel in the handle and shaft of the endoscope, and through the air nozzle at the distal end of the endo scope. Many embodiments described herein may include a cleaning valve (or valve) that is appropriate for single-use and therefore be disposable. Accordingly, the valve may be made from a limited number of parts and materials, e.g., to limit its cost and/or manufacturing complexity. For example, multiple seals may be integrally formed with a valve stem. In another example, the valve may have an interface member (e.g., a cap), which may combine and simplify the functionality of a number of components, such as by connecting the valve stem to a valve well, sealing an opening to a lumen in the valve stem, and/or biasing the valve stem into a position relative to the valve well. In yet another example, the valve stem may be formed with a closed distal end (see e.g., the distal end in FIG. 1B). Enabling the disposability of cleaning valves in an economically viable manner can lead to safer cleaning valves that may minimize or prevent the spread of infection by eliminating or reducing opportunities for germs to be inadvertently introduced into a patient such as due to improper cleaning of a reusable cleaning valve. Further, removing the need of reprocessing cleaning valves between uses can reduce or eliminate staff, verification procedures, processing equipment, time, and/or money needed to perform reprocessing operations.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface used by an operator for operating a valve (e.g., a button) and the term "distal" means a direction away from the surface used by an operator for operating a valve (e.g., a button). Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

Figure 1B:
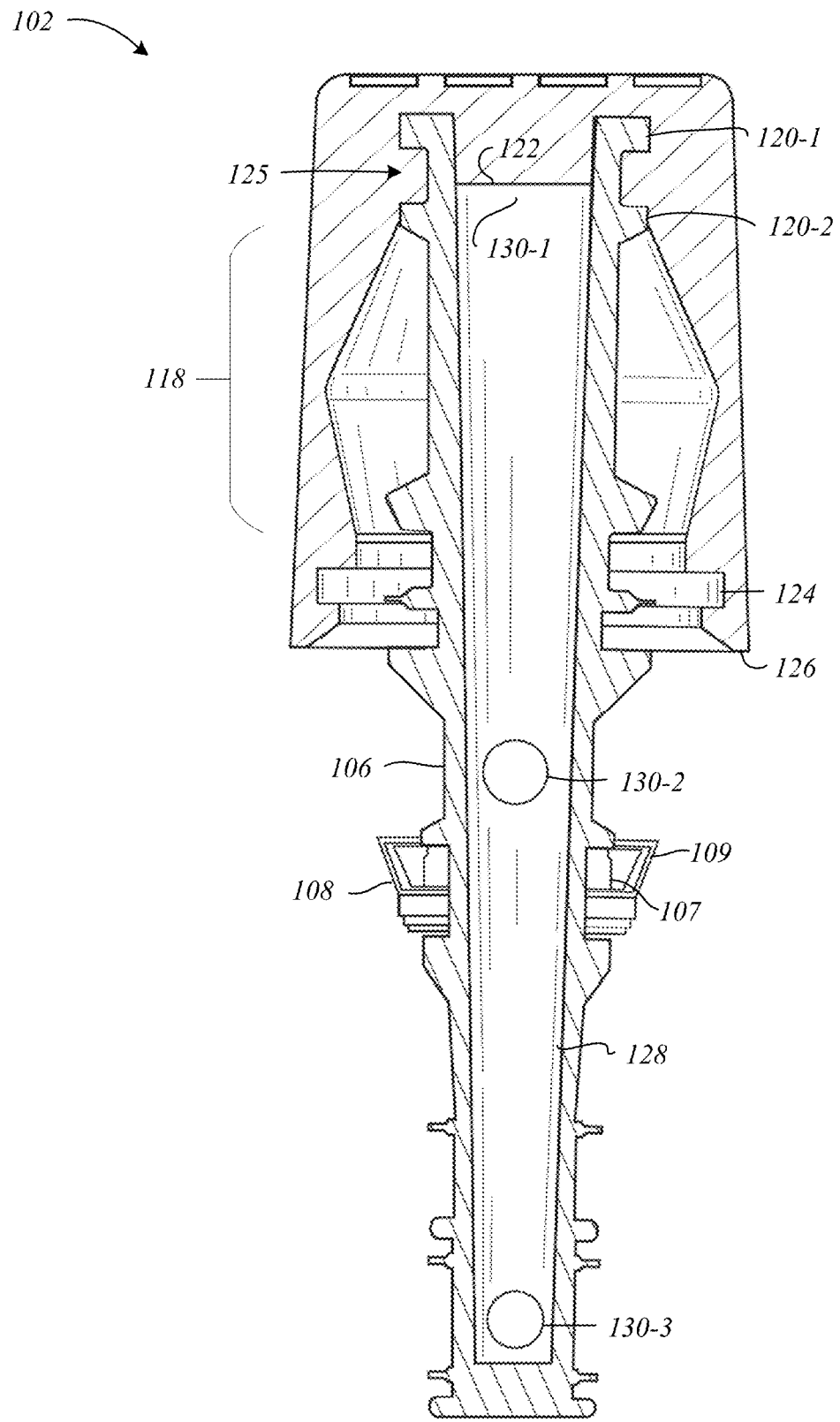
FIG. 1B illustrates a cross-section view of an exemplary cleaning valve according to the present disclosure described herein.

FIGS. 1A and 1B illustrate various aspects of an exemplary cleaning valve 102 according to the present disclosure described herein. More specifically, FIG. 1A illustrates a front view of cleaning valve 102 with a proximal end 145 and a distal end 155 and FIG. 1B illustrates a cross-sectional view of cleaning valve 102 with proximal end 145 and distal end 155. Generally, the cleaning valve 102 may include an interface member 104, a monolithic valve stem 106, and a one-way seal 108. In FIG. 1A, a wireframe version of the interface member 104 is illustrated. As shown in FIG. 1A, the monolithic stem 106 may extend along a longitudinal axis and may include seals seating members 110-1, 110-2 (i.e., seating members 110), seals 112-1, 112-2, 112-3, 112-4 (i.e., seals 112), centering surfaces 114-1, 114-2, 114-3, 114-4 (i.e., centering surfaces 114), and retaining flanges 116-1, 116-2 (i.e., retaining flanges 116) disposed along the longitudinal axis of the monolithic stem 106. As shown in FIG. 1B, the interface member 104 may include a spring portion 118, stem recesses 120-1, 120-2 (i.e., stem recesses 120), stem plug 122, well recess 124, protrusion 125, and retention member 126. Also shown in FIG. 1B, the monolithic stem 106 may include a lumen 128 with orifices 130-1, 130-2, 130-3 (i.e., orifices 130), with orifice 130-1 opening along the longitudinal axis and orifices 130-2, 130-3 extending substantially perpendicular relative to the longitudinal axis of the monolithic stem 106. In one or more embodiments described herein, cleaning valve 102 may be used in cleaning/reprocessing of endoscopes and/or associated equipment, such as at the end of a procedure. Embodiments are not limited in this context.

Figure 2A:
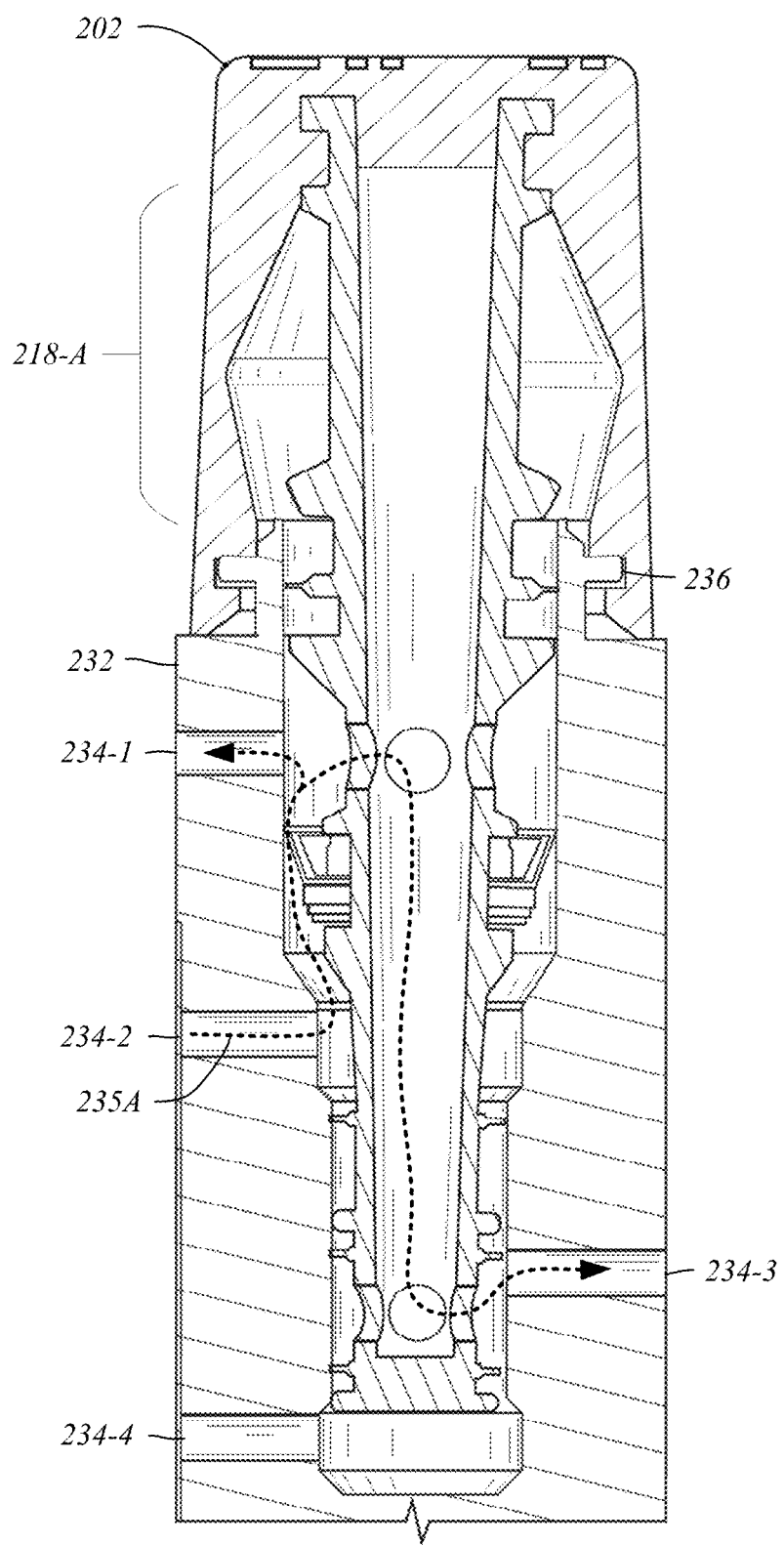
FIG. 2A illustrates a cross-section view of an exemplary cleaning valve and a valve well in a first configuration according to the present disclosure described herein.
Figure 2B:
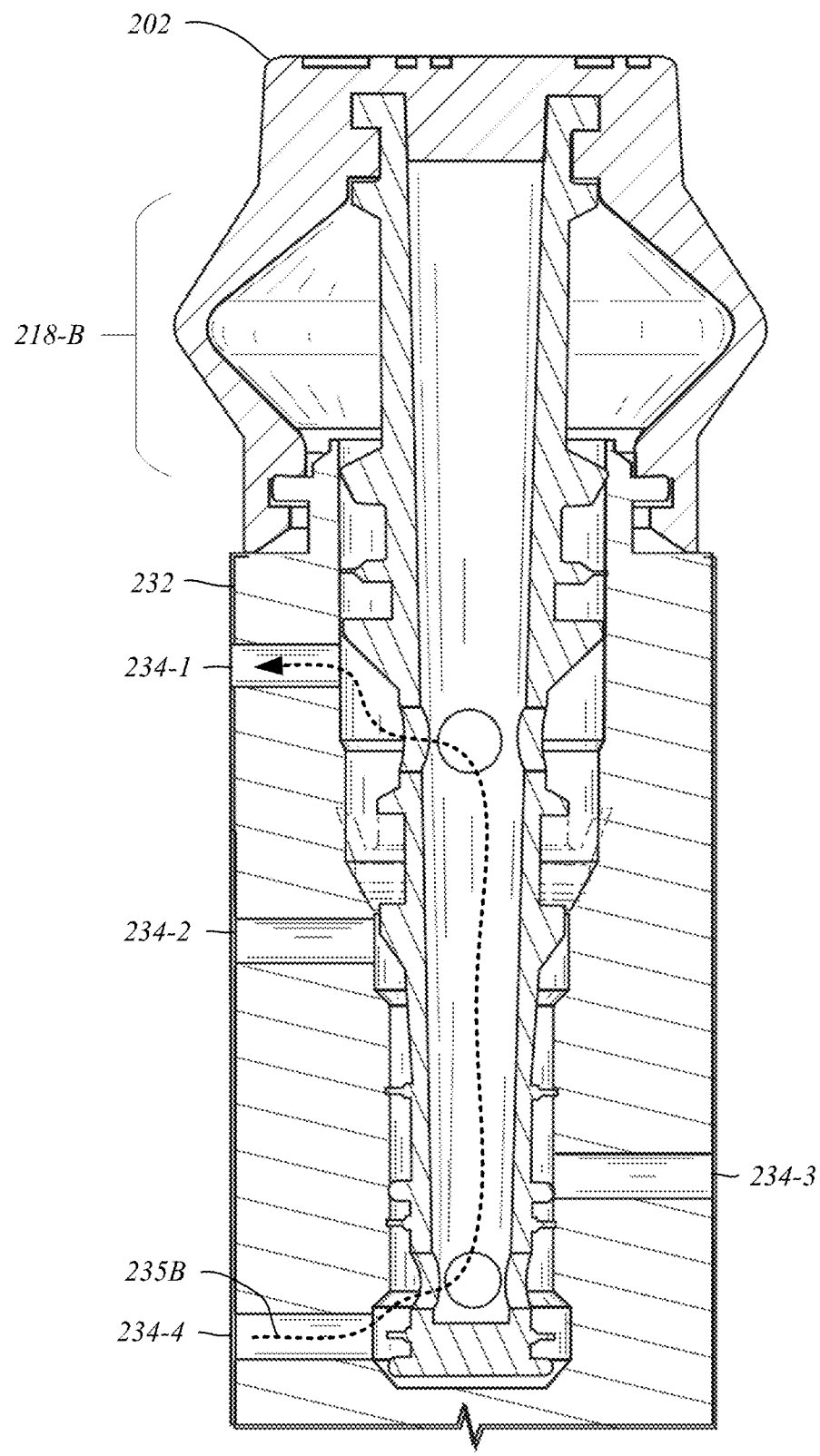
FIG. 2B illustrates a cross-section view of an exemplary cleaning valve and a valve well in a second configuration according to the present disclosure described herein.

In many embodiments, cleaning valve 102 may be insertable into a valve well of an endoscope (e.g., valve well 232 of FIGS. 2A and 2B). In many such embodiments, the interface member 104 may be depressible to cause fluid to flush out and clean portions of the valve well as well as components in fluid communication with the valve well. Many embodiments described herein may include a monolithic valve stem (e.g., monolithic stem 106) that is formed using a forming core pin that is removable via orifice 130-1 at the proximal end 145 of the monolithic stem during manufacturing. In many such embodiments, the orifice 130-1 in then plugged with the stem plug 122 of the interface member 104 when assembled. In various embodiments, the valve stem 106 may be formed with a closed distal end 155 (e.g., have no orifice on the distal end). In this and other ways, the construction and assembly of the cleaning valve 102 may be simplified, such as by minimizing the number of independent parts needed to make the cleaning valve along with minimizing assembly steps for the cleaning valve. Additionally, or alternatively, various embodiments described herein may utilize techniques to create one or more components of the cleaning valve 102 (e.g., seals 112) integrally (e.g., with the same material and/or at the same time) with the monolithic stem 106, such as to minimize the number of independent parts needed to make the cleaning valve along with minimizing assembly steps for the cleaning valve.

In many embodiments one or more components of the monolithic stem 106, such as one or more of the seating members 110, seals 112, centering surfaces 114, retaining flanges 116, lumen 128, and orifices 130 may be integrally formed as a unitary structure. In other words, in several embodiments, the monolithic stem 106 may include a valve stem and one or more additional components that are formed as a unitary structure. For example, lumen 128 may be created with a forming core pin (or core pin) during manufacturing. In such examples, the forming core pin may be used as a support and/or manipulation member as other components of the monolithic stem 106 are formed. Further, the forming core pin may be removed via orifice 130-1. In another example, the monolithic stem 106 may include a valve stem with one or more seals (e.g., seals 112) and/or flanges (e.g., centering surfaces 114 or retaining flanges 116) that are formed as a unitary structure.

Figure 5A:
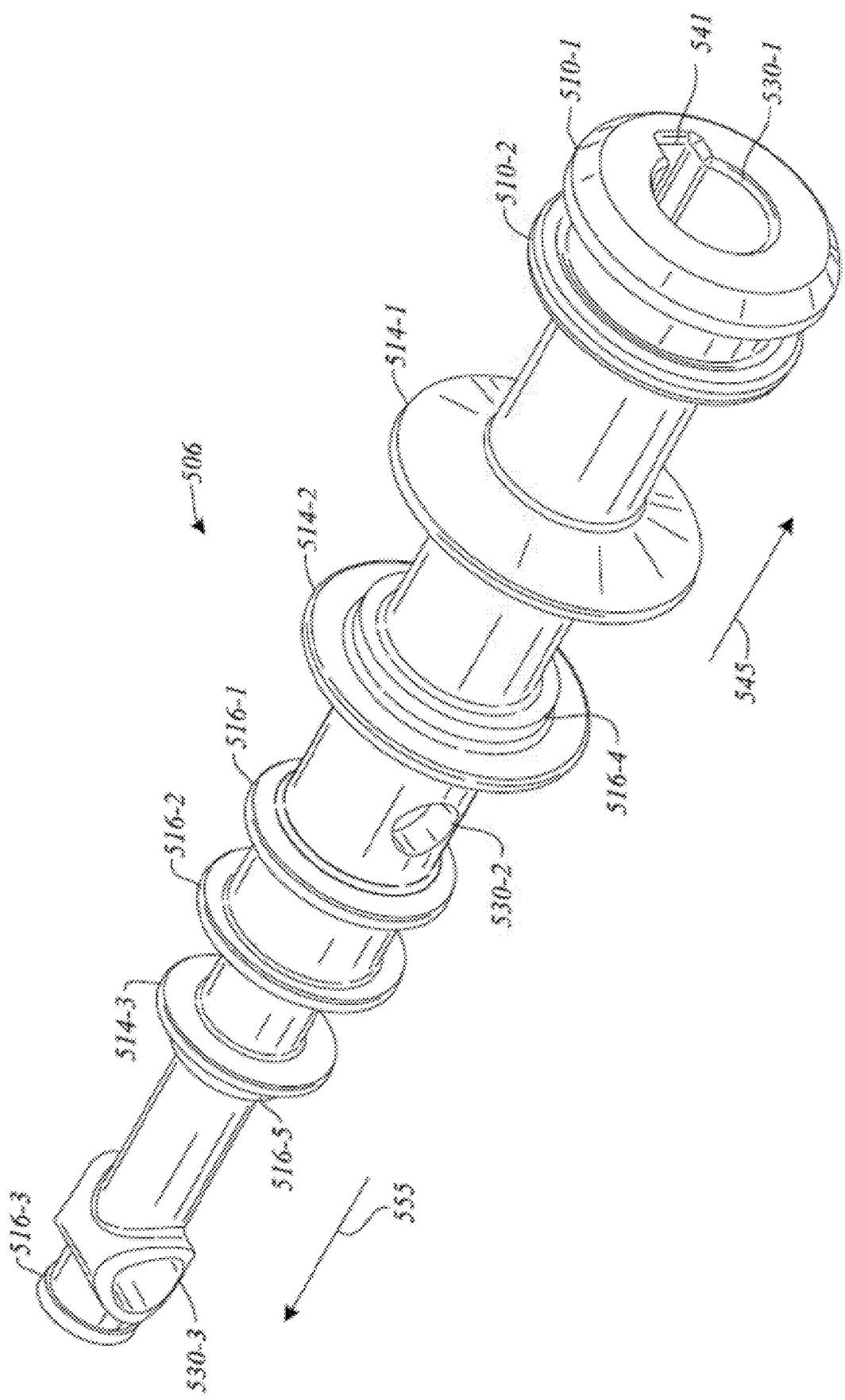
FIGS. 5A-5C illustrate various aspects of an exemplary valve stem according to the present disclosure described herein.

Thus, in many embodiments described herein, the use of "monolithic stem" may include a valve stem that is integrally formed with at least one seal and/or at least one flange, regardless of whether other seals and/or flanges are integrally formed with the valve stem (see e.g., FIG. 5A). However, one or more of the stem-forming and valve assembly features described herein (e.g., a stem formed using a forming core pin that is removable via an orifice at a proximal end of the stem, and then plugged with a stem plug of an interface member) may be utilized with stems that are not monolithic stems (e.g., a stem assembled from two pieces), or with stems that are partially monolithic (e.g., a first portion of the stem is integrally formed with one or more seals and/or flanges, and a one or more seals and/or flanges for a second portion of the stem are not integrally formed with the second portion of the stem). In one embodiment, only the stem itself may be monolithically formed. Accordingly, in some embodiments, the monolithic stem may not be integrally formed with any seals and/or flanges.

In some embodiments, one or more aspects of the interface member 104 and/or the one-way seal 108 may additionally, or alternatively, be formed as part of the monolithic stem 106. In one or more embodiments, different materials may be used during formation of the monolithic stem 106. In various embodiments, some components of the cleaning valve 102 may be assembled onto, overmolded, and/or formed via additional processing of the monolithic stem 106. For instance, one or more of the seals 112 may be overmolded and/or assembled onto the monolithic stem 106. In such instances, one or more of the seals 112 may be formed separately from another material and then assembled onto the monolithic stem 106, or overmolded directly onto the monolithic stem 106.

In the illustrated embodiment of FIGS. 1A and 1B, each of the seating members 110, seals 112, centering surfaces 114, retaining flanges 116, lumen 128, and orifices 130 are integrally formed as part of the monolithic stem 106. The seating members 110 may comprise circumferential protrusions that define a channel therebetween. When assembled, the seating members 110-1, 110-2 may fit, at least partially, into stem recesses 120 of the interface member 104, respectively. Further, the protrusion 125 of the interface member 104 may fit, at least partially, into the channel defined between seating members 110 of the valve stem. Accordingly, in some embodiments, the interface member 104 and monolithic stem 106 may be attached together via a snap fit. In some such embodiments, the snap fit may be a snap interference fit. It is understood that the proximal end of the stem and the interface member may have any interlocking or mating features (e.g., protrusions, recesses, or the like) for attachment.

Similarly, the well recess 124 and retention member 126 of the interface member 104 may be used to connect the cleaning valve 102 to a valve well via a corresponding circumferential protrusion of the valve well (e.g., connection flange 236 of valve well 232 in FIG. 2A). The connection between the interface member 104 of cleaning valve 102 may be a snap fit and/or a snap interference fit. The retaining flanges 116 of monolithic stem 106 may comprise circumferential protrusions that define a channel therebetween for receiving the one-way seal 108. As will be appreciated, numerous techniques for attaching interface member 104 to monolithic stem 106, one-way seal 108 to monolithic stem 106, and/or cleaning valve 102 to a valve well may be utilized without departing from the scope of this disclosure. In many embodiments, the interface member 104 may comprise a cap. In some embodiments, one or more of the retaining flanges 116 may provide a centering surface instead of, or in addition to, one or more of the centering surfaces 114.

As shown in FIG. 1B, one-way seal 108 may include an inner core 107 and an outer rim 109. In various embodiments, one-way seal 108 may include one or more features to prevent the outer rim 109 from inverting during use. For example, one-way seal 108 may include one or more bridges connecting the outer rim 109 to the inner core 107. In another example, one or more ribs may be attached to the outer rim 109. In some examples, the one or more ribs and/or bridges may be attached to an outer rim with a uniform thickness. In yet another example, the thickness of the outer rim 109 may be varied. In various embodiments, the height of the one or more bridges and/or ribs may be a portion of the height of the inner core 107 and/or outer rim 109. For instance, the one or more bridges and/or ribs may be the same height or half the height of the inner core 107 and/or outer rim 109. In many embodiments, the ribs and/or bridges may be aligned with the longitudinal (and/or a radial) axis of the valve stem 106. In one or more embodiments, the ribs and/or bridges may be angled with respect to the longitudinal (and/or a radial) axis of the valve stem 106. In various embodiments, the one or more ribs and/or bridges may be disposed about the circumference of the inner core 107. For instance, the one or more ribs and/or bridges may be equally-spaced (or unequally-spaced) about the circumference of the inner core 107.

In various embodiments, the spring portion 118 of interface member 104 may be used to facilitate transition of the cleaning valve 102 from a first configuration to a second configuration when installed into a valve well. For example, the first configuration may be a standby state and the second configuration may be a flushing state. In some embodiments, the spring portion 118 may bias the cleaning valve into one of the first and second configurations. For instance, the spring portion 118 may bias the cleaning valve 102 into the standby state and the cleaning valve 102 may be transitioned into the flushing state by depressing the interface member 104 toward the distal end 155. This and other aspects of different configurations of the cleaning valve 102 will be described in more detail below, such as with respect to FIGS. 2A and 2B.

The centering surfaces 114 of monolithic stem 106 may comprise circumferential protrusions used to properly align the cleaning valve 102 with a valve well (e.g., valve well 232 of FIG. 2A) of an endoscope. In many embodiments, the centering surfaces 114 may be sized for a slight clearance fit with the inside diameter of the valve well. In various embodiments, the centering surfaces 114 may ensure one or more of the components (e.g., seals) are aligned for proper functionality. For example, centering surfaces 114-3, 114-4 may ensure seals 112-3, 112-4 are properly aligned to create a seal with a valve well. In several embodiments, one or more of the centering surfaces 114 may include one or more features, such as sloped transitions or rounded edges, to guide the cleaning valve 102 into alignment with the valve well.

In the illustrated embodiment, centering surfaces 114-1, 114-2 may have a first diameter and centering surfaces 114-3, 114-4 may have a second diameter. In such embodiments, centering surfaces 114-1, 114-2 may facilitate proper alignment of the cleaning valve 102 with a first diameter of a valve well and centering surfaces 114-3, 114-4 may facilitate proper alignment of the cleaning valve 102 with a second diameter of the valve well (see e.g., FIG. 2A). Further, one or more of the flanges 116 and/or centering surfaces 114 may be used to facilitate an overmolding procedure. For example, seals 112-3, 112-4 may be formed with an overmolding procedure and centering surfaces 114-3, 114-4 may be used during the overmolding procedure to retain flow from the overmolding procedure from running proximal of centering surface 114-3 and/or distal of centering surface 114-4.

The seals 112 may comprise a wiper blade seal geometry. In several embodiments, the wiper blade seal geometry may be used in combination with a lubricious and/or flexible material, such as a polymer (e.g. polycarbonate, acrylonitrile butadiene styrene (ABS), high-density polyethylene (HDPE), Nylon, polyether ether ketone (PEEK), thermoplastic, plastic, or the like). In many embodiments, the seals 112 may include a thin portion or wiper portion that deforms when introduced into a valve well. In several embodiments, the seals may form a slight interference fit with the valve well. For instance, the wiper portion may deflect proximally while also compressing radially inward such that it may slide into an inner diameter of the valve well and keep contact with the valve well to seal fluid from passing longitudinally past the seal in either direction. In various embodiments, wiper seals may be used to accommodate greater manufacturing tolerances, such as by allowing a wider range of diameters with consistent friction for sealing.

The thin wall geometry may allow for a much more rigid material, such as HPDE, to be used, which can also facilitate formation of the seal from the same material as the monolithic stem. For example, the nominally thicker wall of the lumen may provide adequate rigidity and strength to the monolithic stem during use while the thinner wall of at least a portion of the seal provides adequate flexibility for the seals. This and other aspects of the monolithic stem 106 will be described in more detail below, such as with respect to FIGS. 3A-3C.

The lumen 128 of monolithic stem 106 may comprise a channel placing the one or more of the orifices 130 in fluid communication. In the illustrated embodiment, the lumen 128 places orifices 130-2, 130-3 in fluid communication and the stem plug 122 of interface member 104 seals orifice 130-1 and prevents fluid from escaping via orifice 130-1. The distal end of the lumen 128 may be enclosed or sealed by a portion of the monolithic stem 106.

In various embodiments, the orifices 130 may include one or more axial and/or one or more radial holes. For example, orifice 130-1 may comprise an axial hole and each of orifices 130-2, 130-3 may comprise respective radial through-holes spaced about the circumference of the valve stem 106. In other embodiments, for example, different numbers of radial through-holes may be utilized, such as two crisscross radial through-holes for each of orifices 130-2, 130-3. As will be described in more detail below, in various embodiments, the orifices 130-2, 130-3 may allow fluid to pass from the outside diameter of the monolithic stem to the lumen 128 in the inner diameter.

FIGS. 2A and 2B illustrate various configurations of an exemplary cleaning valve 202 in conjunction with an exemplary valve well 232 of an endoscope according to the present disclosure described herein. More specifically, FIG. 2A illustrates a first configuration of the cleaning valve 202 in conjunction with valve well 232 and FIG. 2B illustrates a second configuration of the cleaning valve 202 in conjunction with valve well 232. The first configuration may include a standby state (e.g., loaded into valve well 232, but not depressed by a user) while the second configuration may include a flushing state (e.g., loaded into valve well 232 and depressed by a user). In many embodiments, one or more components illustrated in FIGS. 2A and 2B may be the same or similar in construction, function, and/or appearance as one or more other components described herein. For example, cleaning valve 202 may be the same or similar to cleaning valve 102. Embodiments are not limited in this context.

FIGS. 2A and 2B include cleaning valve 202 and valve well 232. In FIG. 2A, cleaning valve 202 is illustrated with spring portion 218-A, which may correspond to the first configuration. In FIG. 2B, cleaning valve is illustrated with spring portion 218-B, which may correspond to the second configuration. In both FIGS. 2A and 2B, valve 232 comprises inlets 234-1, 234-2, 234-3, 234-4 (i.e., inlets 234) disposed along a longitudinal axis of the valve well 232 and connection flange 236. In various embodiments, during a procedure using the valve well 232 (e.g., a procedure on a patient creating the need to clean/reprocess with cleaning valve 202) inlet 234-1 may serve as an air outlet, inlet 234-2 may serve as an air inlet, inlet 234-3 may serve as a water outlet, and inlet 234-4 may serve as a water inlet. As used herein, inlet does not indicate a direction of flow, accordingly, a fluid may flow into or out of an inlet. As previously mentioned, connection flange 236 may include a circumferential protrusion that facilitates cleaning valve 202 snap fitting onto the valve well 232.

In various embodiments, in the first configuration (e.g., the standby state), the cleaning valve 202 is loaded into the valve well 232, but not depressed (e.g., by a user). The interface member may snap and/or engage with the valve well 232 to hold the cleaning valve 202 in the valve well 232 against a positive system pressure. A pump may be pumping a fluid (e.g., air or CO2) into inlet 234-2. As illustrated by the flow arrow 235A in FIG. 2A, in the first configuration, fluid may flow through cleaning valve 202 and valve well 232 as follows. The fluid may be diverted proximally past the one-way seal (e.g., the seal is able to radially compress inward due to the pressure of the fluid, the thin wall of the one-way seal, and the orientation of the one-way seal). The fluid may then pass out of the valve well 232 via inlet 234-1, as well as, into the lumen of the monolithic stem through an orifice (e.g., orifice 130-2), down the lumen, and out the lower orifice (e.g., orifice 130-3) before exiting the valve well 232 via inlet 234-3. Further, in the first configuration, inlet 234-4 is blocked off due to the distal most seal position (e.g., seal 112-4).

In the second configuration (e.g., the flushing state), the valve may be depressed by a user and inlet 234-2 is closed off, blocked by seal 112-2 distally and the one-way seal bottoming out on the well inside diameter proximally so there is no flow. In this configuration, inlet 232-4 is opened due to the seal movement at the distal end, which, as illustrated by the flow arrow 235B in FIG. 2B, allows water to flow into the distal stem fluid orifice (e.g., orifice 130-3 comprising four radial holes), up the lumen and out of the proximal fluid orifice (e.g., orifice 130-2) where it then is forced out of inlet 234-1. It is blocked by the proximal most wiper seal (e.g., seal 112-1) from exiting the valve well and also blocked from traveling distally via the one-way seal. It will be appreciated that, although not illustrated for simplicity, the flows 235A, 235B may travel circumferentially between the interior of the valve well 232 and the exterior of the monolithic stem 106 to enter/exit each of the plurality of holes comprising the orifices. In various embodiments, the one-way seal 1862 may be constructed from a TPE, such as Versaflex CL2250®. In some embodiments, the one-way seal 1862 may be clear/translucent.

Figure 3A:
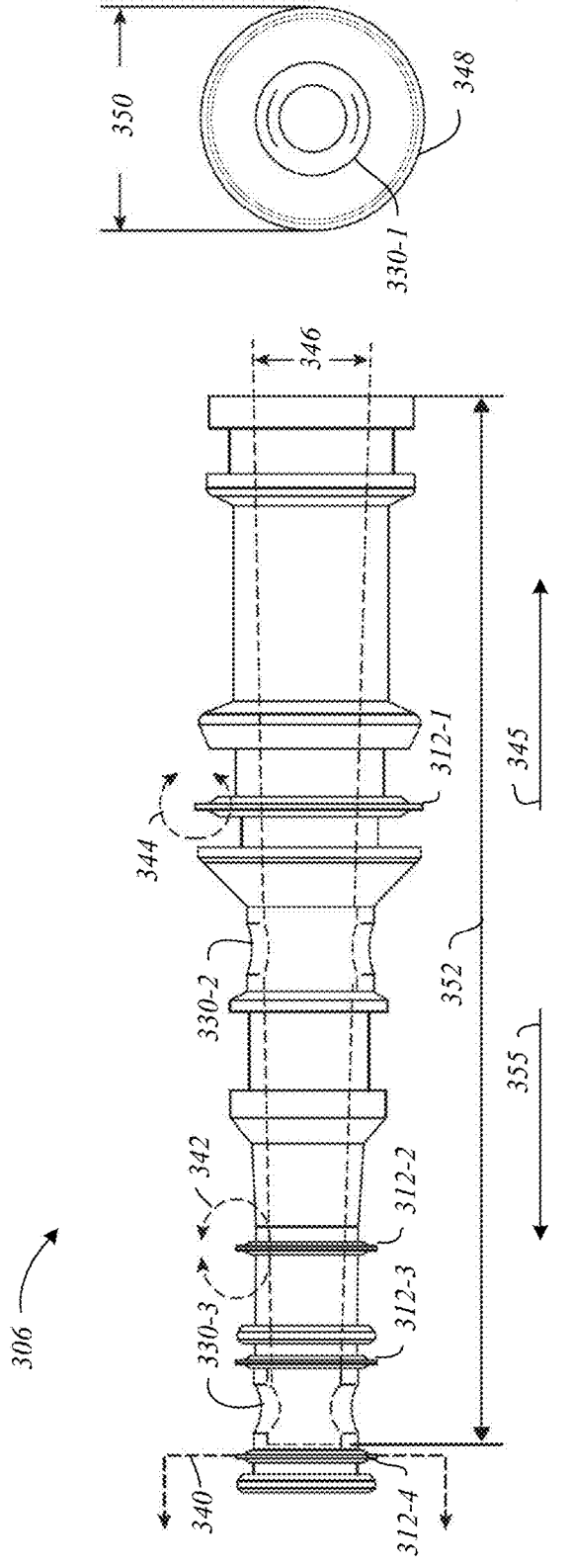
FIGS. 3A-3C illustrate various aspects of an exemplary monolithic valve stem according to the present disclosure described herein.
Figure 3B:
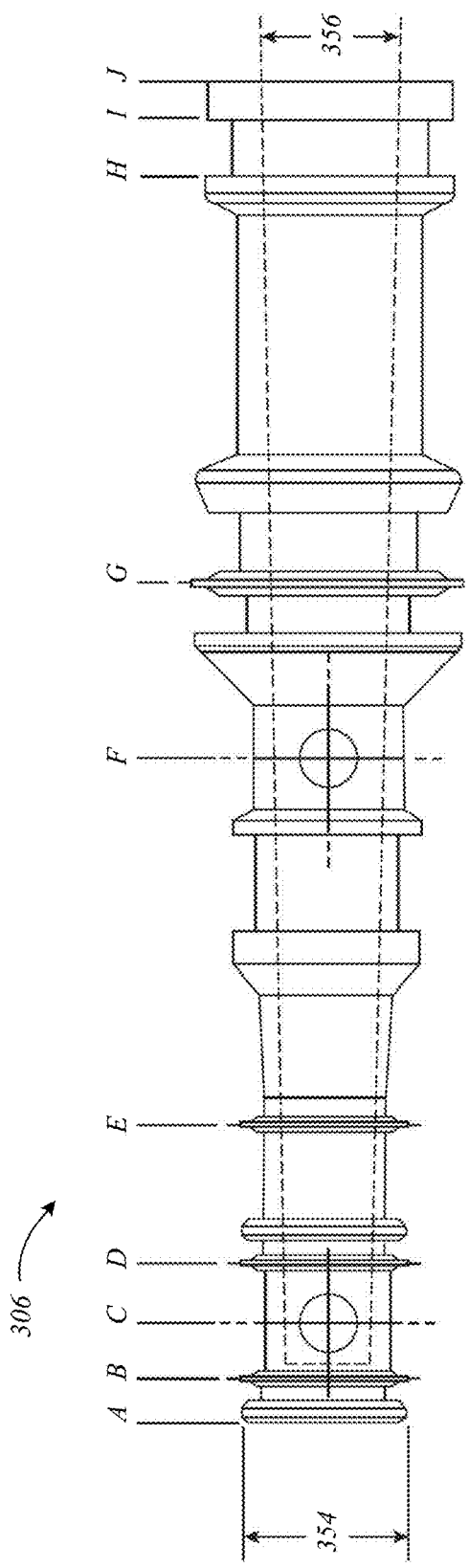
Figure 3C:
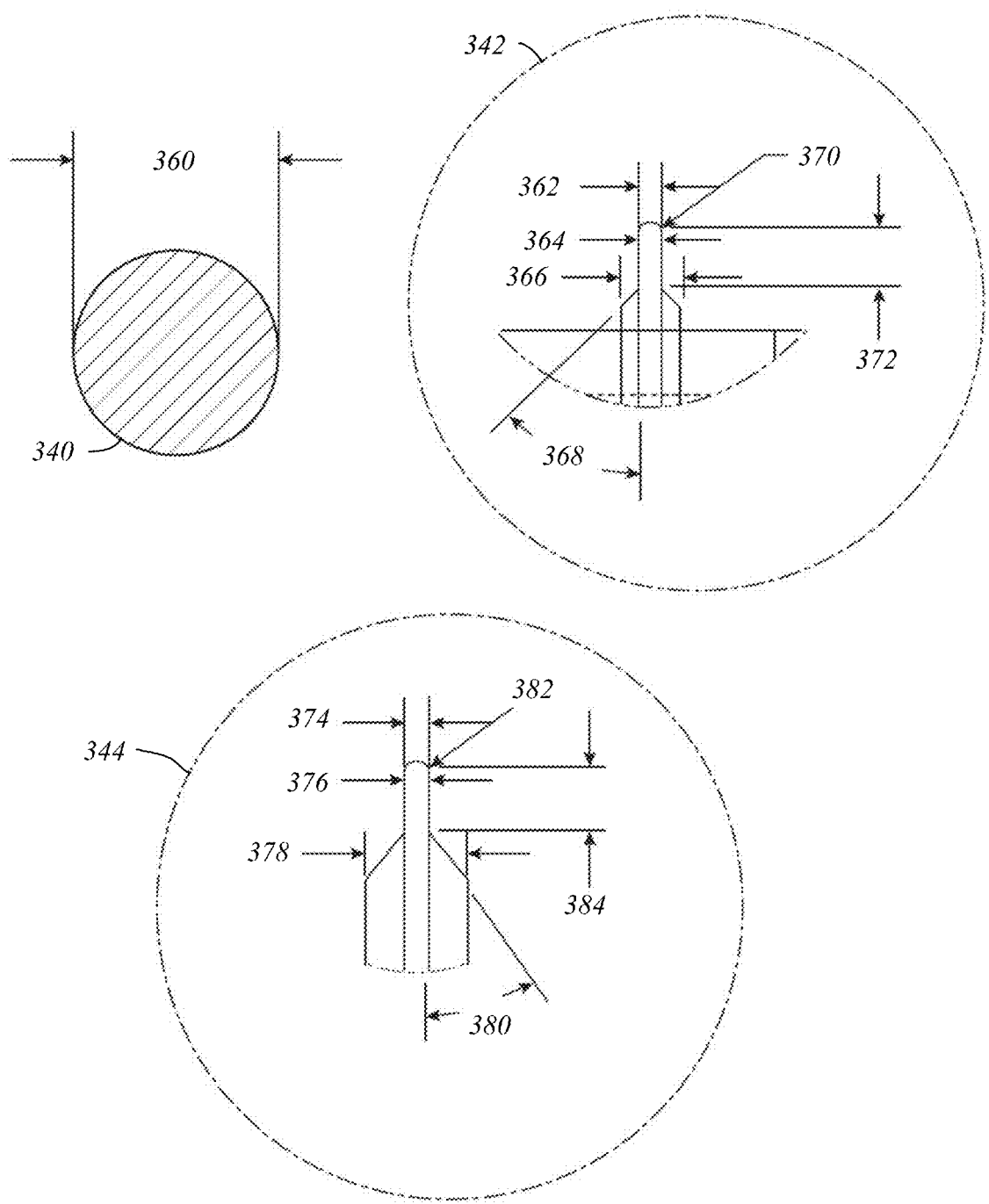

FIGS. 3A-3C illustrate various aspects of an exemplary monolithic stem 306 according to the present disclosure described herein. FIG. 3A illustrates a first side view of the monolithic stem 306. The monolithic stem 306 may include orifices 330-1, 330-2, 330-3, seals 312-1, 312-2, 312-3, 312-4, a proximal end 345, and a distal end 355. FIG. 3A also includes a front view 348 of the proximal end 345 of monolithic stem 306. FIG. 3B illustrates a second side view of the monolithic stem 306. FIG. 3C illustrates a cross-section 340 of the monolithic stem 306 at the seal 312-4, a profile 342 of the seal 312-2 (which may be representative of seals 312-2, 312-3, 312-4), and a profile 344 of the seal 312-1. In many embodiments, one or more components illustrated in FIGS. 3A-3C may be the same or similar in construction, function, and/or appearance as one or more other components described herein. For example, monolithic stem 306 may be the same or similar to monolithic stem 106. Embodiments are not limited in this context.

Referring to FIG. 3A, the monolithic stem 306 may include a proximal end 345 and a distal end 355. The cross-section 340 and profiles 342, 344 are illustrated in FIG. 3C. The distance 352 between the cross-section 340 and the proximal end 345 of the monolithic stem 306 may be between 1.25 and 2.25 inches. For example, the distance 352 may be 1.77 inches. The diameter between opposite walls of the lumen may increase from the distal end 355 to the proximal end 345. Accordingly, diameter between opposite walls of the lumen may increase between the proximal and distal ends 345, 355 with an angle 346 between 0 and 10 degrees. For example, the angle 346 may be three degrees. In various embodiments, the increase in diameter from the distal end 355 to the proximal end 345 may facilitate efficient removal of the core pin through the proximal end 345 of the monolithic stem 306.

In many embodiments, the seals 312 may extend beyond corresponding bearing surfaces of the monolithic stem 306. This may cause the seals 312 to have a slight interference fit with the interior of a valve well. The slight interference fits may create wiper seals with the interior of the valve well to control fluid flow through the valve well while still allowing the monolithic stem 306 to slide up and down in the valve well. In many embodiments, seal 312-1 may have a first set of dimensions while seals 312-2, 312-3, 312-4 share a second set of dimensions. For example, seals 312-2, 312-3, 312-4 may have a first diameter and seal 312-1 may have a second diameter. In many such embodiments, the second diameter is larger than the first diameter.

As shown in the front view 348 of the proximal end 345 of the monolithic stem 306, the seal 312-1 may have a diameter 350. The diameter 350 may be between 0.25 and 0.75 inches with a tolerance between 0 and 0.01 inches. For instance, the diameter 350 may be 0.382 inches with a tolerance of +/-0.003 inches. The front view 348 of the proximal end 345 of the monolithic stem 306 also shows the orifice 330-1. In many embodiments, the orifice 330-1 may be plugged by an interface member (e.g., interface member 104 of cleaning valve 102). Referring to FIG. 3C, as shown in the cross-section 340, seal 312-4 (which may be representative of seals 312-2, 312-3 too) may have a diameter 360. The diameter 360 may be between 0.175 and 0.3 inches with a tolerance between 0 and 0.01 inches. For instance, the diameter 360 may be 0.242 inches with a tolerance of +/-0.003 inches. Still referring to FIG. 3C, profile 344 illustrates various dimensions of the seal 112-1 while profile 342 illustrates various dimensions of the seal 312-2 (which may be representative of seals 312-3, 312-4 too).

Profile 342 may include dimensions 362, 364, 366, 368, 370, 372. Dimension 362 may include a thickness proximate an outer extent of the seal 312-2. In some embodiments, dimension 362 may be between 0.002 and 0.01 inches. For example, dimension 362 may be 0.006 inches. Dimension 364 may include an angle at which an outer portion of the seal 312-2 narrows. In various embodiments, dimension 364 may be between 0 and 10 degrees. For instance, dimension 364 may be two degrees. Dimension 366 may include a thickness of an inner portion of the seal 312-2. In many embodiments, dimension 366 may be between 0.01 and 0.03 inches. For example, dimension 366 may be 0.02 inches.

Dimension 368 includes an angle of change at a transition from an inner portion thickness to an outer portion thickness of the seal 312-2. In some embodiments, dimension 368 may be between 15 and 75 degrees. For instance, dimension 368 may be 45 degrees. Dimension 370 includes a radius of the outer extend of the seal 312-2. In several embodiments, dimension 370 may be between 0.001 and 0.006 inches. For example, dimension 370 may be 0.003 inches. Dimension 372 includes a width of the outer portion of the seal 312-2. In various embodiments, dimension 372 may be between 0.01 and 0.03 inches. For instance, dimension 372 may be 0.02 inches.

Profile 344 may include dimensions 374, 376, 378, 380, 382, 384. Dimension 374 may include a thickness proximate an outer extent of the seal 312-1. In some embodiments, dimension 374 may be between 0.002 and 0.01 inches. For example, dimension 374 may be 0.006 inches. Dimension 376 may include an angle at which an outer portion of the seal 312-1 narrows. In various embodiments, dimension 376 may be between 0 and 10 degrees. For instance, dimension 376 may be two degrees. Dimension 378 may include a thickness of an inner portion of the seal 312-1. In many embodiments, dimension 378 may be between 0.02 and 0.04 inches. For example, dimension 378 may be 0.03 inches. Dimension 380 includes an angle of change at a transition from the inner portion to the outer portion of the seal 312-1. In some embodiments, dimension 380 may be between 10 and 70 degrees. For instance, dimension 380 may be 35 degrees. Dimension 382 includes a radius of the outer extend of the seal 312-1. In several embodiments, dimension 382 may be between 0.001 and 0.006 inches. For example, dimension 382 may be 0.003 inches. Dimension 384 includes a width of the outer portion of the seal 312-1. In various embodiments, dimension 384 may be between 0.01 and 0.03 inches. For instance, dimension 384 may be 0.02 inches.

Referring back to FIG. 3B, the dimension 354 may be a diameter of the distal end 355 of the monolithic stem 306. In various embodiments, dimension 354 may be between 0.15 and 0.35 inches. For example, dimension 354 may be 0.231 inches. In such examples and when the diameter of seals 312-2, 312-3, 312-4 are 0.24 inches, the seals 312-2, 312-3, 312-4 may extend beyond the bearing surfaces at 0.0045 inches along their circumference. Further, this extension beyond the bearing surfaces may facilitate formation of the previously mentioned wiper seals with a valve well.

Dimension 356 may include a diameter of orifice 330-1 at the proximal end 345 of the monolithic stem 306. In some embodiments, dimension 356 may be between 0.13 and 0.25 inches. For instance, dimension 356 may be 0.192 inches. Additionally, FIG. 3B may include reference points A-J. Reference point A may be the distal end 355 of the monolithic stem 306. Reference point B may be the seal 312-4 and the distance between reference points A and B may be between 0.05 and 0.07 inches, such as 0.06 inches. Reference point C may be the center of orifice 330-3 and the distance between reference points A and C may be between 0.10 and 019 inches, such as 0.14 inches. Reference point D may be the seal 312-3 and the distance between reference points A and D may be between 0.20 and 0.24 inches, such as 0.22 inches. Reference point E may be the seal 312-2 and the distance between reference points A and E may be between 0.37 and 0.45 inches, such as 0.41 inches. Reference point F may be the center of orifice 330-2 and the distance between reference points A and F may be between 0.90 and 0.95 inches, such as 0.918 inches. Reference point G may be the seal 312-1 and the distance between reference points A and G may be between 1.11 and 1.21 inches, such as 1.16 inches. Reference point H may be the proximal extent of a seating member (e.g., seating member 110-2) and the distance between reference points A and H may be between 1.69 and 1.76 inches, such as 1.721 inches. Reference point I may be the distal extent of a seating member (e.g., seating member 110-1) and the distance between reference points A and I may be between 1.7 and 1.9 inches, such as 1.8 inches. Reference point J may be the proximal end 345 of the monolithic stem 306 and the distance between references points A and J may be between 1.75 and 1.95 inches, such as 1.851 inches.

With reference to profiles 342, 344 of FIG. 3C, the profile of the seals may facilitate one or more functionalities of the seals. In many embodiments, the combination of a relatively thick base with a relatively thin outer rim allows the seal to function in a pressurized system. For example, the thin outer rim of the seals can provide the required flexibility while the transition to the thicker base closer to the outside diameter of the stem resists deformation. This may be done in order to maintain the appropriate radially opposing force at the end of the seals to maintain contact with the wall of the valve well even when the contents (e.g., fluid) it is sealing against becomes pressurized.

As previously mentioned, in various embodiments, the stem is able to be one monolithic component with the seals built into it. Accordingly, one or more seals described herein can eliminate processing steps, the number of materials used, as well as assembly complexity, thus reducing cost of the overall cleaning valve. In several embodiments, a core pin may be used to create the lumen of the monolithic stem 306. Further, the core pin may be used to manipulate (e.g., position and reposition) the monolithic stem 306 during formation. The lumen may fluidly connect the orifices to allow for fluid (e.g., liquid or gas) flow through the lumen of the monolithic stem. However, the core pin may leave an orifice (e.g., orifice 330-1) in the monolithic stem for removal of the core pin (e.g., in the proximal end) that needs to be plugged to constrain fluid flow between the radial orifices (e.g., orifices 330-2, 330-3) of the stem. In various embodiments, this orifice may be plugged via the interface member, which may be formed of silicone, thermoplastic elastomer (TPE), or some other flexible material that can be used to form an interference snap fit over the proximal end of the stem.

A cap, such as one with conformable material and an interference fit (e.g., interface member 104), can act as a seal at the proximal end of the stem once assembled thereon (e.g., via stem plug 122). This seal may prevent leaks at the proximal end of the stem during use. Some alternative methods of sealing with alternative components could include press fitting a plug of the same material as the stem into the end of the stem. In various embodiments, the plug could remain in place due to the press fit, or it could be ultrasonically welded, glued or any other fastening method.

In some embodiments, the one-way seal can be loaded over the monolithic stem and fit into the receiving well on the stem, such as via a snap fit, or the one-way seal could be overmolded (e.g., from silicone, TPE, or some other flexible material) directly onto the stem as a secondary process. In various embodiments, one or more of the seals 312 may be formed/assembled in the same or similar manner. In some embodiments, one or more surface treatments may be applied to the monolithic stem 306. For example, one or more surface treatments may be used to clean and/or lubricate the monolithic stem 306. In various embodiments, one or more components may be plugged and/or masked prior to surface treatments. For instance, the orifices 330 may be plugged prior to a lubricating surface treatment.

In one or more embodiments described herein, various ranges, tolerances, dimensions, and/or ratios thereof may be selected to suit particular applications. For example, tighter tolerances may be required for gas valve applications than liquid valve applications. In some embodiments, these selections may facilitate and/or optimize one or more functionalities described herein. For instance, accurate dimensions may ensure proper fit into a valve well. In another example, tolerances may ensure operational temperature swings can be accommodated. In yet another example, accurate dimensions may ensure proper function of wiper seals. In still another example, accurate ratios may ensure efficient flow through lumens. In still another example, accurate ratios, tolerances, and/or dimensions may ensure proper operation of the spring portion of an interface member (e.g., valve position and/or tactile feedback). Accordingly, utilizing one or more ranges, dimensions, and tolerances described herein (and/or ratios thereof) may provide components with reliable operation and/or economical manufacture.

Figure 4C:
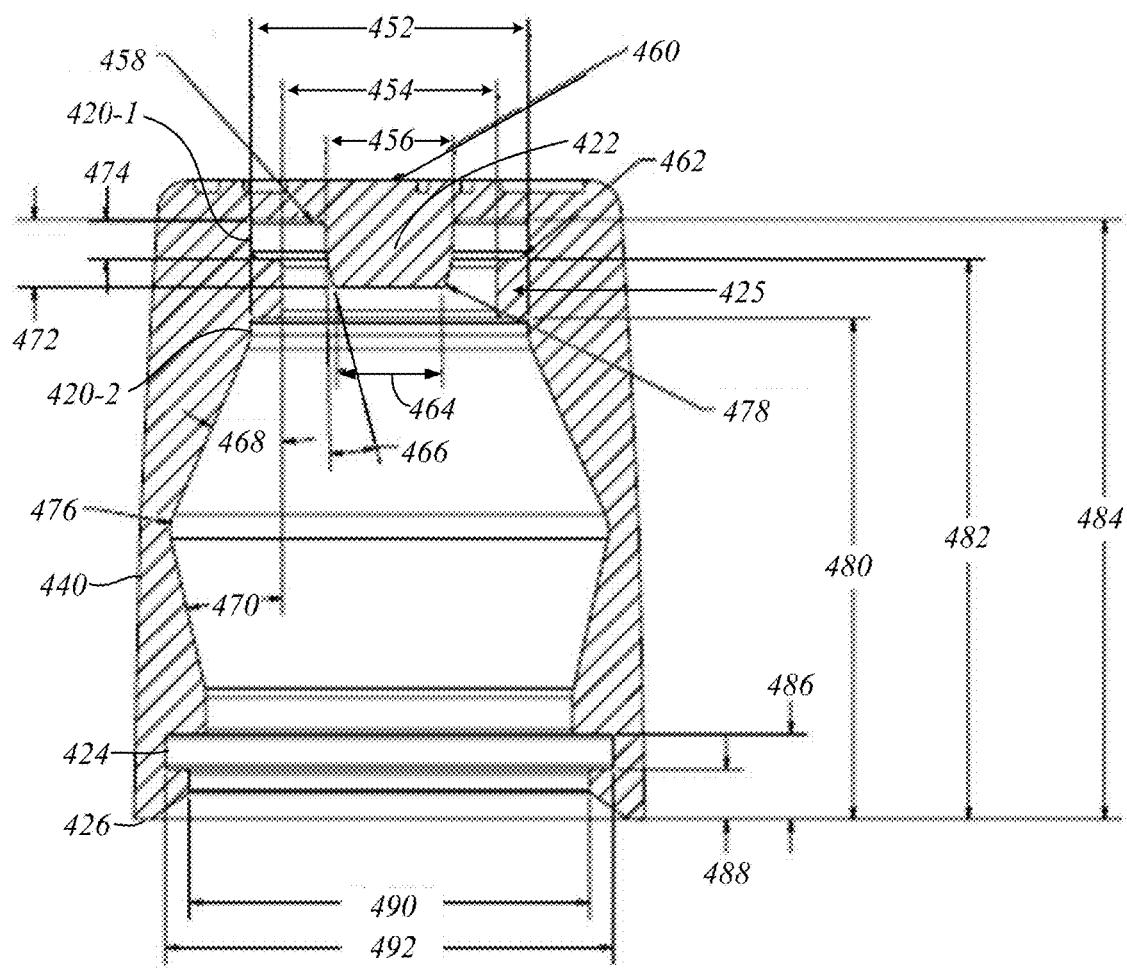

FIGS. 4A-4C illustrate various aspects of an exemplary interface member 404 according to the present disclosure described herein. FIG. 4A illustrates a perspective view of the interface member 404. FIG. 4B illustrates a side view of the interface member 404. FIG. 4C illustrates a cross-section 440 of the interface member 404. In many embodiments, one or more components illustrated in FIGS. 4A-4C may be the same or similar in construction, function, and/or appearance as one or more other components described herein. For example, interface member 404 may be the same or similar to interface member 104. Accordingly, interface member 404 may include a spring portion 418, stem recesses 420-1, 420-2, a stem plug 422, a well recess 424, a protrusion 425, a retention member 426, a proximal end 445, and a distal end 455. Additionally, as will be described in more detail below, the interface member 404 may include an indicator 443. Embodiments are not limited in this context.

Referring to FIG. 4A, the interface member may include indicators 443. In the illustrated embodiment, indicators 443 include an exclamation point enclosed by a triangle, e.g., as a raised, indented, or embossed surface, or combinations thereof. More generally, cleaning valves may include one or more indicators on one or more components. In various embodiments, indicators (e.g., indicator 443) may serve to communicate, through operation or aesthetics, one or more characteristics of a cleaning valve. Accordingly, one or more of the cleaning valves disclosed herein may include features and/or components to facilitate differentiation from procedural valves (i.e., valves for use in a procedure performed on a patient). Further, the features and/or components described herein may be used in any combination to facilitate differentiation from procedural valves. For example, the feel and/or look may be varied from a procedural valve, including a differentiation in shape, color, material, and other visual and/or tactile indicators. In another example, an additional component, such as an indicator, may be included to facilitate differentiation from procedural valves.

The feel of a valve may be important to where the user will recognize the valve as something they are conditioned to use in a procedure or if the valve is something that feels substantially different than what they are used to. Oftentimes, different valves (for example, both an air/water valve, as well as a suction valve) are designed to look and feel substantially similar. This may be done such that the physician does not interpret any tactile difference between different available valves. However, this may lead to confusion between cleaning and procedural valves, which can lead to adverse outcomes. Accordingly, embodiments described herein may have a substantially different feel to the user than a procedural valve, in order to minimize potential incorrect use, e.g., to make it apparent to a user if a procedure is started with the cleaning valve in the air/water valve well rather than the procedural air/water valve. For example, the characteristics of the spring portion 418 of an interface member may provide a substantially different tactile feedback than a procedural valve.

In various embodiments, the interface member or user interface portion (e.g., button or spring cap) of the valve may be constructed out of a substantially different material. For example, a soft, tacky, and/or flexible material such as a silicone elastomer or thermoplastic elastomer (TPE) may form a softer and/or tackier user interface or interface member surface of the valve that interacts with a user (e.g., finger/hand of the user). In such examples, this soft, tacky, and/or more flexible feel may differentiate the cleaning valve from more rigid molded plastic valve buttons of procedural valves. In a further example, the raised portions of indicators 443 may have a tacky feel.

In many embodiments, features may be added to the user interface of the valve to differentiate the feel of the valve when compared to procedural valves. Procedural valves typically have substantially smooth, flat, circular user interface surfaces that interact with a user when the valves are depressed. However, one or more embodiments described herein may have user interface surfaces that feel substantially different when depressing the valve. For example, the user interface surface may include a multitude of small protrusions from the surface in the form of cones, rods, bumps, loops, ridges, or any other three-dimensional textured surface that can cause the user to notice they are not pressing on a smooth surface.

In several embodiments, the user interface (e.g., button or spring cap) may be shaped to differentiate the feel of the cleaning valve when compared to procedural valves. For example, the user interface may include a geometric shape to interact with the user that has pronounced corners that could be felt during depression of the user interface, such as a circle, triangle, square, rhombus, hexagon, or any other shape that would have a distinct or pronounced edge when compared to a circle. When depressed these shapes may feel substantially different than a circular button used on procedural valves with a smooth radius on the edge of the valve.

In some embodiments, the user interface (e.g., button or spring cap) may be sized to facilitate distinction from procedural valves. Many procedural valves are roughly half an inch in diameter on the user interface surface (e.g., proximal side of the button). However, adjusting the size of the user interface surface the user presses to be substantially larger or substantially smaller can allow the user to notice a size difference in the surface they are pressing, further differentiating the cleaning valve from the procedural valve. This size difference may include one or more of the surface area of the user interface surface being depressed, as well as the height that the surface sits above the endoscope handle when inserted into the air/water well. For instance, a substantially shorter or substantially taller surface may result in the user to move their hands/fingers in a manner that they are not used to in order to operate the valve, again drawing further attention to the fact that this is not a typical procedural valve. For optimal differentiation, a valve may include any combination of the above-mentioned features and/or techniques of differentiating the look and/or feel of a cleaning valve from procedural valves.

In several embodiments, the look or appearance of a cleaning valve may be used to differentiate the feel of the valve when compared to procedural valves. Many procedural valves are primarily all black buttons, with a cylindrical collar that snaps onto the valve well and a cylindrical button with a flat button surface. By substantially changing the appearance of the cleaning valve from a procedural valve, a user may have their attention better drawn to it when they see one inserted in the air/water valve well of an endoscope handle. The appearance of the cleaning valve may be differentiated by including one or more of the following.

In some embodiments, color selection of one or more components of the cleaning valve may be used to differentiate the look of the cleaning valve when compared to procedural valves. In many embodiments, the colors may be selected to provide contrast to the black endoscope handle and/or black procedural valves that blend in with the endoscope handle. For example, using one or more bright or neon colors, such as yellow, orange, red, and pink, on one or more components of a cleaning valve assembly may be used to differentiate the valve visually. In another example, a clear or "natural" silicone elastomer color or TPE color may be used. This clear color may leave a translucent appearance that is clearly noticeable when looking at the valve in an endoscope handle. In some embodiments, reflective or glitter surfaces may be used.

Differentiating the valve by feel may also differentiate the valve by look. For instance, changing the shape of the valve user interface (e.g., button or spring cap) from circular to some other geometric shape would allow for visual differentiation in addition to feel differentiation, especially when combined with a substantially different color/pattern like described above. Making the interface a triangle shape, square shape, rhombus shape, hexagonal, or any other shape with sharp angular edges may provide visual and tactile differentiation of the valve from a circular procedural valve.

Typically, air/water and suction procedural valves used (whether disposable or re-usable versions) may have the same combination of a button surface to be depressed which slides inside of a collar component that attaches to the scope. By changing this configuration such that the same two components with the same type of interaction are no longer present may further help differentiate a cleaning valve from procedural valves. In various embodiments, switching the way the button component and collar component interact may be used to differentiate the valve. For example, the button may be a skirt that slides over the outside of the collar component. In such examples, this may change the overall shape of the user interface significantly compared to the button of procedural valves. In some embodiments, the shape and component interaction may be changed to eliminate separate button and collar components altogether, such as by having a single seamless spring cap that both connects to the valve well as well as the top of the valve stem fully enclosing the entire valve from the outside. This, along with a soft flexible material, and/or different colors may substantially differentiate the valve from procedural valves.

In several embodiments, an indicator (e.g., warning) of some kind may be included in or on the valve (e.g., valve stem 106). For example, ways of including a warning on the valve for differentiating a cleaning valve from a procedural valve could include pad printing or laser etching a warning directly onto the user interface (e.g., spring cap or button) or exposed surface of the cleaning valve during use. Alternatively, or additionally, a warning label could be embossed on the side of the user interface (e.g., spring cap or button), providing a warning that protrudes out from the side of the valve and is felt and clearly visible during use. This could be located on the side of the valve, or on the top surface forcing the user to feel the warning when they depress the valve. Alternatively, or additionally, a warning tag could be molded into the cap and integrally attached as part of the component. As will be appreciated, the text and/or symbols may be varied (as long as they facilitate differentiation from a procedural valve) without departing from the scope of this disclosure.

In addition, or alternatively, to the cap color, the color of one or more other components may be changed to differentiate from a procedural valve. For example, the valve stem color may be substantially different than procedural valve stems. In some embodiments, the seal colors can be a bright color (e.g., yellow) on the stem, or a combination of any other colors, that draws the attention of a user to the fact that the valve is for cleaning. As well, the valve stem itself can be colored or patterned substantially different than the procedural valves, which may be a stainless-steel natural color. In various embodiments, a combination of natural color elastomer spring cap, with natural color seals and a yellow stem may be used, but any distinct combination such as yellow stem and seals, blue seals and yellow stem, pink stem and yellow seals, etc. may be used. Additionally, the cap could have a raised feature molded in, such as circumferentially around its base, and/or have pad printing circumferentially with writing indicating a warning or some type of instructions for use. In many embodiments, the user may be able to read a warning on the cap without actually having to have a separate warning tag attached as it would be directly printed or visible as part of the cap itself.

In many embodiments, there may be an additional component that slides over or removably attaches to the seal end of the valve stem in the packaging with a shape that prevents the valve from being inserted into the valve well of the endoscope without the additional component first being removed. In many embodiments, a portion of this component may be inserted through a radial hole of the valve stem. In various embodiments, this component may clip to the valve stem. In some embodiments, this component could be hollow with an inside diameter large enough to slide over the end of the valve stem and an outside diameter large enough such that it has an interference fit with the valve well on the scope so it is unable to be inserted.

In various embodiments, this component could be a molded component made of a bright color material to further draw attention to it. In many embodiments, it must be removed from the valve prior to being able to insert the valve into the endoscope. This may ensure the user must complete an additional step prior to being able to insert the cleaning valve into the endoscope further drawing attention that the valve is not a procedure valve. This component could also be a clip style component that clips onto the valve stem from the side, again causing interference with the valve well if a user attempts to insert the valve prior to removal. The clip tag or the tag that slides over the end of the valve stem could also have a molded tag off the side with embossed lettering or pad printed lettering. In some embodiments, this verbiage could also act as a warning tag, not only informing the user of the intended "cleaning" use, but also requiring the user to remove the warning prior to insertion in the valve well, forcing them to focus their attention on it for some time prior to attempting to insert the valve into the scope. As will be discussed in more detail below, several exemplary indicators, including many described above, are illustrated in FIGS. 7A-7G.

Referring to FIG. 4C, the cross-section 440 of interface member 404 includes stem recesses 420-1, 420-2, stem plug 422, well recess 424, protrusion 425, and retention member 426. The dimensions (e.g., distances, widths, radii, diameters, angles, and the like) are described with respect to components herein in the absence of external input (e.g., in the first configuration). The diameter 452 of each stem recess 420-1, 420-2 may be between 0.3 and 0.4 inches, such as 0.348 inches with a tolerance of ±0.003. The height 474 of stem recess 420-1 may be between 0.025 and 0.075 inches, such as 0.05 inches. The interior diameter 454 of the protrusion 425 may be between 0.22 and 0.31 inches, such as 0.269 inches with a tolerance of ±0.003. The diameter 456 of a proximal portion of the stem plug 422 may be between 0.13 and 0.19 inches, such as 0.16 inches. The distal end of the stem plug 422 may have a diameter between 0.1 and 0.2 inches, such as 0.132 inches.

The stem plug 422 may transition from the first to the second diameter with an angle 466 between 10 and 25 degrees, such as 14 degrees. The outside corner 478 may have a radius between 0.0025 and 0.0075 inches, such as 0.005 inches. The height 472 of stem plug 422 may be between 0.05 and 0.13 inches, such as 0.085 inches. The corner 458 between the stem recess 420-1 and stem plug 422 may have a radius between 0.005 and 0.015 inches, such as 0.01 inches. The corner 462 between the stem recess 420-1 and protrusion 425 may have a beveled or chamfered edge. For example, corner 462 may have a 0.01 inch by 45 degree chamfer. One or more edges, bends, walls, and/or corners (inside or outside) described herein may have a bevel, chamfer, radius, and/or fillet with selected characteristics, such as based on whether the corner is used for flexing, receiving, and/or retaining.

The height 484 from the distal end of the interface member 404 to the proximal extent of the stem recess 420-1 may be between 0.72 and 0.80 inches, such as 0.76 inches. The height 482 from the distal end of interface member 404 to the distal extent of the stem recess 420-1 may be between 0.68 and 0.74 inches, such as 0.71 inches. The height 480 from the distal end of interface member 404 to the proximal extent of stem recess 420-2 may be between 0.60 and 0.67 inches, 0.635 inches. The radial deflection 468 of the proximal portion of spring portion 418 may be between 14 and 36 degrees, such as 24 degrees. The radial deflection 470 of the distal portion of spring portion 418 may be between 5 and 21 degrees, such as 13 degrees. The radius 476 at the transition between the proximal and distal portions of spring portion 418 may be between 0.02 and 0.1 inches, such as 0.05 inches.

Figure 5B:
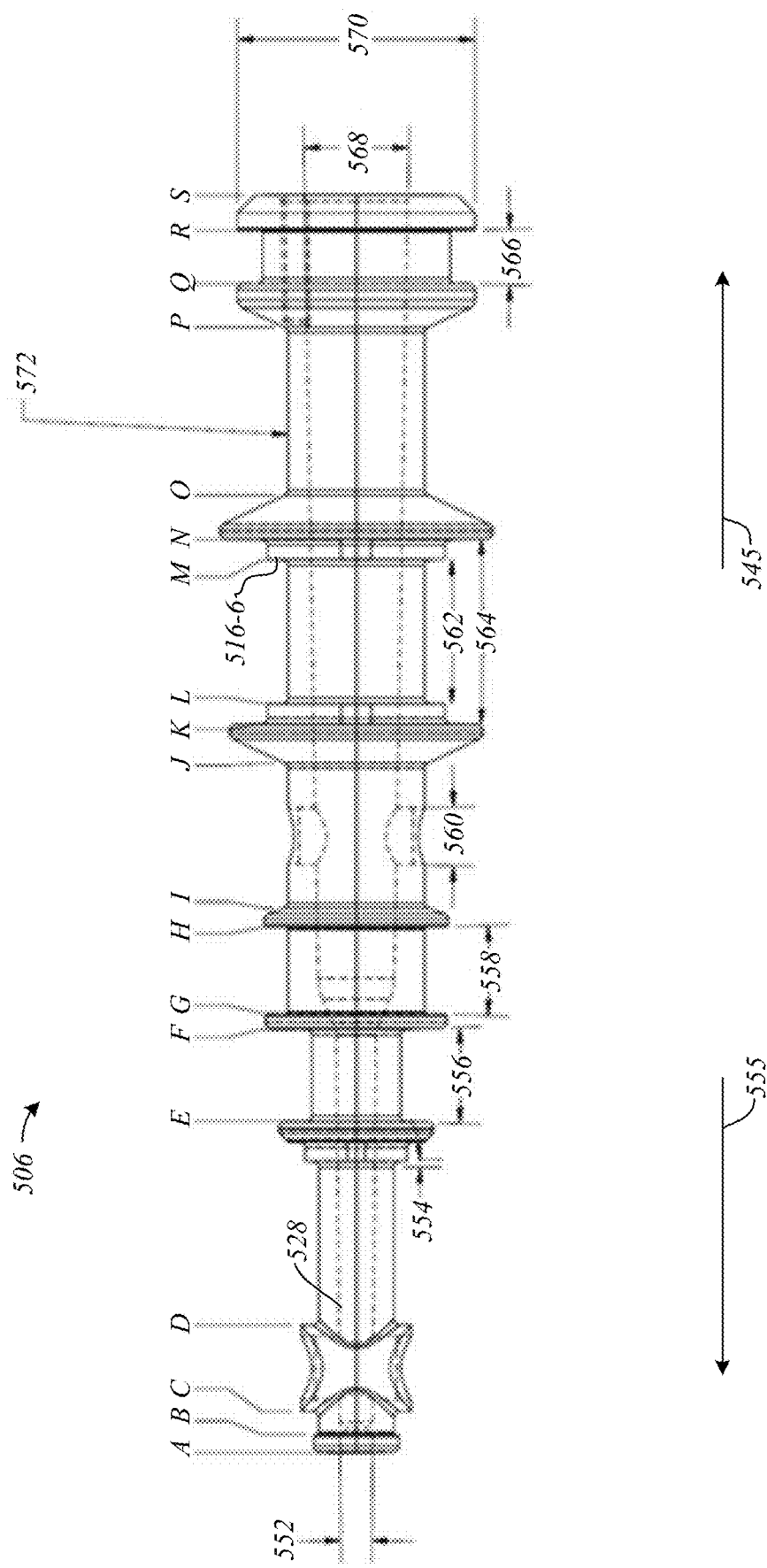
Figure 5C:
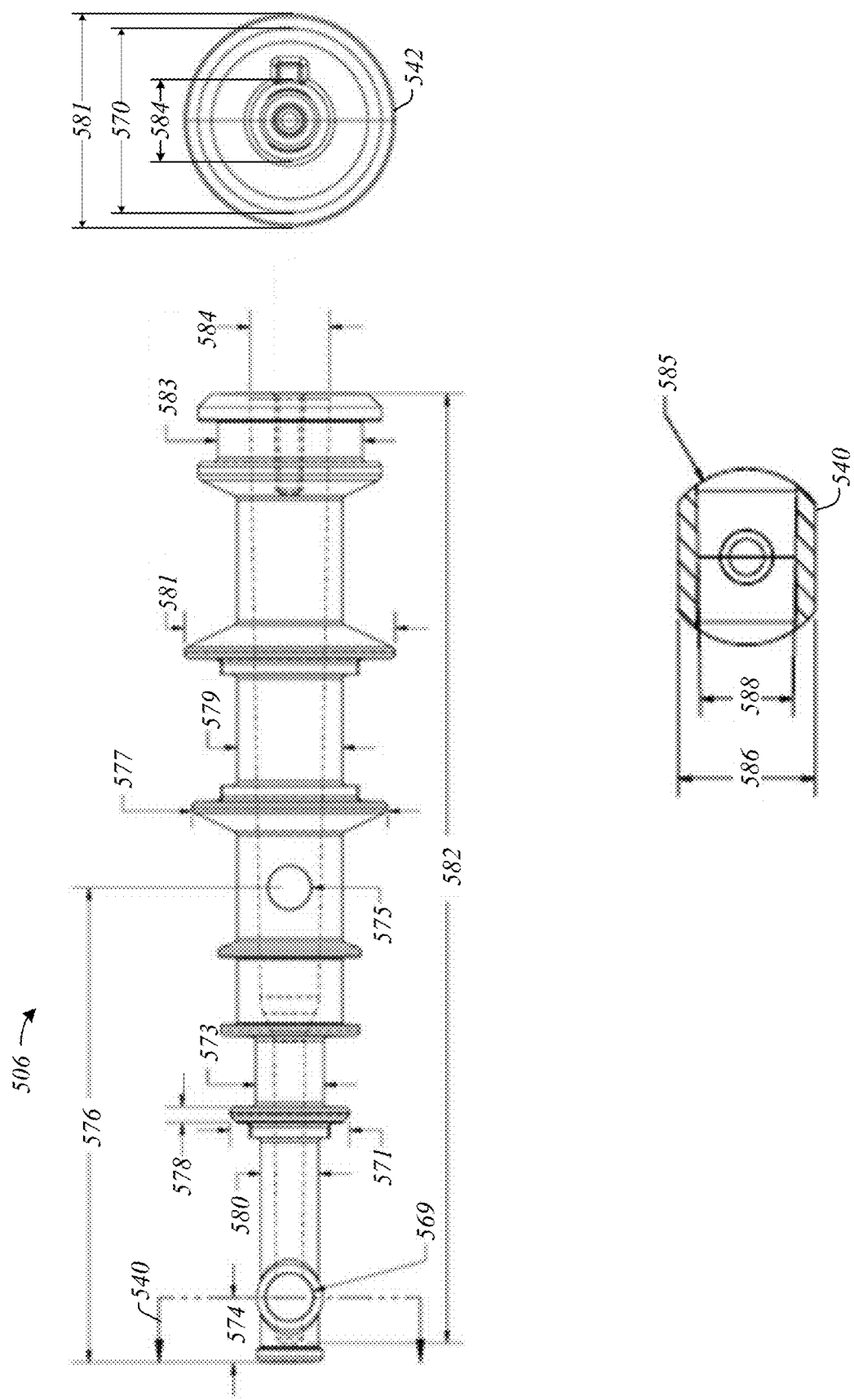

The diameter 492 of the well recess 424 may be between 0.51 and 0.63 inches, such as 0.562 inches. The height 486 from the distal end of the interface member 404 to the proximal extent of the well recess 424 may be between 0.09 and 0.12 inches, such as 0.108 inches. The height 482 from the distal end of interface member 404 to the distal extent of the well recess 424 may be between 0.057 and 0.069 inches, such as 0.063 inches. The inner diameter 490 of retention member 426 may be between 0.48 and 0.52 inches, such as 0.502 inches. FIGS. 4B and 4C, or one or more other embodiments described herein, may be interpreted in accordance with American Society of Mechanical Engineers Y14.5M-2009 standard. The material of interface member 404 may include one or more of elastosil, liquid silicone, rubber, (e.g., with a hardness between 25 and 75 durometers, such as 50 durometers). In many embodiments, internal corner radii may be a maximum of 0.15 inches. In various embodiments, the external surfaces may have an SPI-d1 finish. Rounding radii may be 0.005 inches unless otherwise noted FIGS. 5A-5C illustrate various aspects of an exemplary valve stem 506 according to the present disclosure described herein. FIG. 5A illustrates a perspective view of the valve stem 506. The valve stem 506 may include a proximal end 545, a distal end 555, seating members 510-1, 510-2, centering surfaces 514-1, 514-2, 514-3, retaining flanges 516-1, 516-2, 516-3, 516-4, 516-5, orifices 530-1, 530-2, 530-3. Orifice 530-1 may include a notch 541. FIG. 5B illustrates a first side view of the valve stem 506 with lumen 528 and retaining flange 516-6. FIG. 5C illustrates a second side view of the valve stem 506, a cross-section 540 of the valve stem 506 at the orifice 530-3, and a top view of the proximal end 545 of the valve stem 506. In many embodiments, one or more components illustrated in FIGS. 5A-5C may be the same or similar in construction, function, and/or appearance as one or more other components described herein. For example, seating members 510 may be the same or similar to seating members 110. Embodiments are not limited in this context.

In many embodiments one or more components of the monolithic stem 506, such as one or more of the seating members 510, centering surfaces 514, retaining flanges 516, lumen 528, and orifices 530 may be integrally formed as a unitary structure. In embodiments, components of the valve stem 506 may serve multiple roles. For example, retaining flange 516-2 may also be a centering surface. In another example, seating member 510-2 may also be a retaining flange. In some embodiments, components of a valve stem may be adjacent to and/or in contact with other components. For example, retaining flange 516-4 and centering surface 514-2 are in contact in valve stem 506. Further, centering surface 514-1 may include a mirror retaining flange. In such examples, the two retaining flanges may prevent flow distal of retaining flange 516-4 and proximal of the other retaining flange during an overmolding procedure.

Figure 6C:
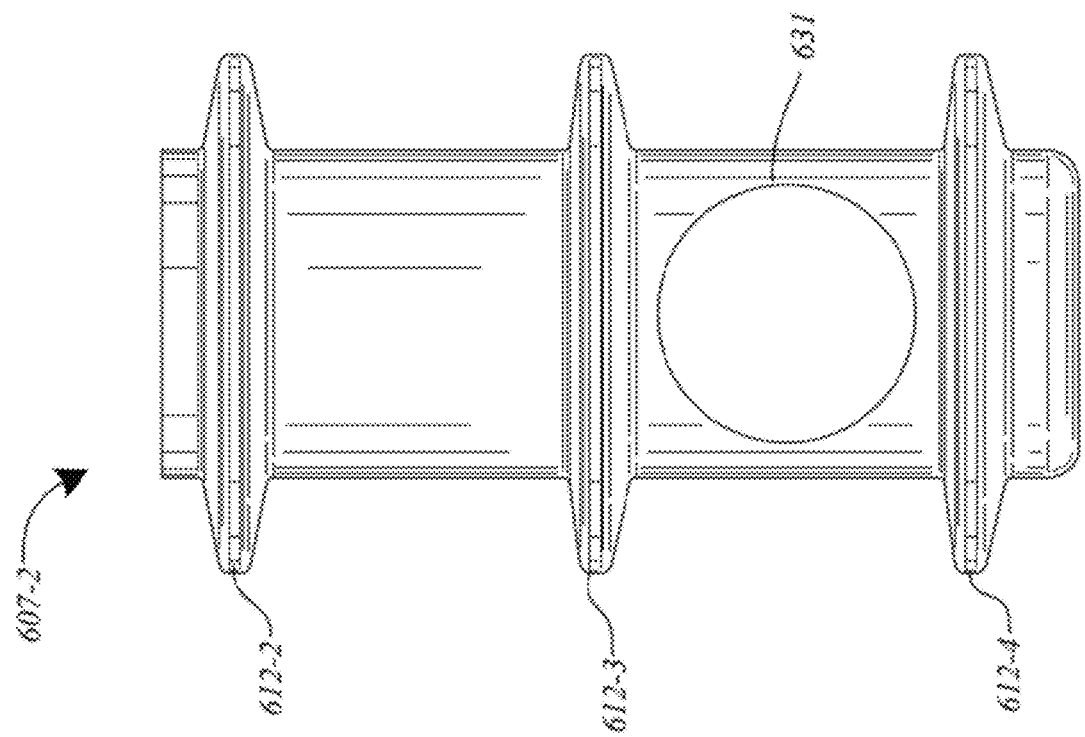

More generally, valve stem 506 may include multiple features, such as ridges, lips, protrusions, channels, and the like, that support overmolding procedures. For example, orifice 530-3 may include a raised lip that prevents flow into the lumen of valve stem 506 during an overmolding procedure. Additionally, or alternatively, one or more of seating members 510, centering surfaces 514, retaining flanges 516, and orifices 530-1, 530-2 may support overmolding procedures. For example, notch 541 may keep the stem 506 aligned on a core forming pin. In various embodiments, notch 541 may facilitate alignment of an interface member that connects to the stem 506. In some embodiments, valve stem 506 may be referred to as a stem or a bare stem while the valve stem assembly 605 of FIG. 6A is referred to as a valve stem. In various embodiments, a stem or bare stem may refer to a valve stem that is missing one or more components, such as overmolded seals, O-rings, and the like. As will be discussed in more detail below, overmolding procedures may be used to form one or more seals along valve stem 506 (see e.g., FIGS. 6B and 6C).

FIG. 5B may include angles 552, 554, 556, 558, 560, 562, 564, 566, 568, dimension 570, and reference points A-S. Angle 552 may be the angle at which the walls of a distal portion of the lumen 528 diverge in the proximal direction. Angle 568 may be an angle at which the walls of a proximal portion of the lumen 528 converge in the distal direction. In various embodiments, the angles 552, 568 may be between 0 and 10 degrees. For example, angle 552 may be 1 degree and angle 568 may be 2 degrees. However, the angle at which the walls of lumen 528 diverge may range between 0 and 90 degrees. For example, at the transition between the proximal and distal portions of lumen 528 (proximate reference point G), the walls may converge at a 45 degree angle. In one or more embodiments, the angles 552, 568 may facilitate efficient and reliable removal of a core forming pin. In various embodiments, dimension 570 may be between 0.25 and 0.4 inches, such as 0.348 inches with a tolerance of ±0.003. In one or more embodiments, element 572 may indicate the gate location for introducing material, such as during an injection molding process to form stem 506.

The angle 554 may be the slope in the radial direction of the distal side of retaining flange 516-3. In various embodiments, the angle 554 may be between 0 and 15 degrees. For example, angle 554 may be 3 degrees. The angle 556 may be the angle in the radial direction between the proximal side of centering surface 514-3 and the distal side of retaining flange 516-2. In various embodiments, the angle 556 may be between 0 and 20 degrees. For example, angle 556 may be 4 degrees. The angle 558 may be the angle in the radial direction between the proximal side of retaining flange 516-2 and the distal side of retaining flange 516-1. In various embodiments, the angle 558 may be between 0 and 20 degrees. For example, angle 558 may be 4 degrees. The angle 560 may be the angle in the radial direction between the walls of the orifice 530-2. In various embodiments, the angle 560 may be between 0 and 10 degrees. For example, angle 560 may be 2 degrees.

The angle 562 may be the angle in the radial direction between the proximal side of retaining flange 516-4 and the distal side of retaining flange 516-6. In various embodiments, the angle 562 may be between 0 and 20 degrees. For example, angle 562 may be 4 degrees. Similarly, the angle 564 may be the angle in the radial direction between the proximal side of centering surface 514-2 and the distal side of centering surface 514-1. In various embodiments, the angle 564 may be between 0 and 20 degrees. For example, angle 564 may be 4 degrees. The angle 566 may be the angle in the radial direction between the proximal side of seating member 510-2 and the distal side of seating member 510-1. In various embodiments, the angle 566 may be between 0 and 10 degrees. For example, angle 566 may be 2 degrees. In some embodiments, negative angles may be used between features, such as to retain, couple, guide, and/or receive another component.

Additionally, FIG. 5B may include reference points A-S. Reference point A may be the distal end 555 of the valve stem 506. Reference point B may be the proximal side of retaining flange 516-3 and the distance between reference points A and B may be between 0.02 and 0.04 inches, such as 0.027 inches. Reference point C may be the distal side of orifice 530-3 and the distance between reference points A and C may be between 0.05 and 0.07 inches, such as 0.06 inches. Reference point D may be the proximal side of orifice 530-3 and the distance between reference points A and D may be between 0.176 and 0.196 inches, such as 0.186 inches.

Reference point E may be the proximal side of centering surface 514-3 and the distance between reference points A and E may be between 0.47 and 0.50 inches, such as 0.482 inches. Reference point F may be the distal side of retaining flange 516-2 and the distance between reference points A and F may be between 0.58 and 0.65 inches, such as 0.616 inches. Reference point G may be the proximal side of retaining flange 516-2 and the distance between reference points A and G may be between 0.60 and 0.68 inches, such as 0.639 inches. Reference point H may be the distal side of retaining flange 516-1 and the distance between reference points A and H may be between 0.74 and 0.79 inches, such as 0.764 inches. Reference point I may be the proximal side of retaining flange 516-1 and the distance between reference points A and I may be between 0.75 and 0.85 inches, such as 0.792 inches.

Reference point J may be the distal side of centering surface 514-2 and the distance between reference points A and J may be between 0.90 and 1.10 inches, such as 1.002 inches. Reference point K may be the proximal side of centering surface 514-2 and the distance between reference points A and K may be between 0.96 and 1.16 inches, such as 1.060 inches. Reference point L may be the proximal side of retaining flange 516-4 and the distance between reference points A and L may be between 0.98 and 1.18 inches, such as 1.089 inches. Reference point M may be the distal side of retaining flange 516-6 and the distance between reference points A and M may be between 1.19 and 1.39 inches, such as 1.298 inches. Reference point N may be the distal side of centering surface 514-1 and the distance between reference points A and N may be between 1.22 and 1.42 inches, such as 1.327 inches.

Reference point O may be the proximal side of centering surface 514-1 and the distance between reference points A and O may be between 1.29 and 1.49 inches, such as 1.392 inches. Reference point P may be the distal side of seating member 510-2 and the distance between reference points A and P may be between 1.53 and 1.73 inches, such as 1.635 inches. Reference point Q may be the proximal side of seating member 510-2 and the distance between reference points A and Q may be between 1.59 and 1.79 inches, such as 1.699 inches. Reference point R may be the distal side of seating member 510-1 and the distance between reference points A and R may be between 1.67 and 1.87 inches, such as 1.777 inches. Reference point S may be the proximal end 545 of the valve stem 506 and the distance between references points A and S may be between 1.72 and 1.92 inches, such as 1.828 inches.

FIG. 5C illustrates, a second side view of the valve stem 506, a cross-section 540 of the valve stem 506 at the orifice 530-3, and a top view of the proximal end 545 of the valve stem 506. The distance 574 between the cross-section 540 and the distal end 555 of the valve stem 506 may be between 0.05 and 0.23 inches. For example, the distance 352 may be 1.77 inches. The outer diameter 580 of valve stem 506 may be between 0.05 and 0.23 inches. For example, the outer diameter 580 may be 1.77 inches. The width 578 of centering surface 514-3 may be between 0.01 and 0.058 inches. For example, the width 578 may be 0.029 inches. The outer diameter 571 of the centering surface 514-3 may be between 0.1 and 0.31 inches. For example, the outer diameter 571 may be 0.227 inches. The outer diameter 573 of valve stem 506 may be between 0.05 and 0.27 inches. For example, the outer diameter 580 may be 0.13 inches.

The diameter 575 of orifice 530-2 may be between 0.05 and 0.22 inches, such as 0.83 inches. The distance 576 from the distal end of the valve stem 506 to the center of orifice 530-2 may be between 0.7 and 0.12 inches, such as 0.896 inches. The outer diameter 577 of centering surface 514-2 may be between 0.3 and 0.42 inches, such as 0.371 with a tolerance of +/−0.003 inches. The diameter 579 of valve stem 506 may be between 0.17 and 0.23 inches, such as 0.2 inches. The outer diameter 581 of centering surface 514-1 may be between 0.35 and 0.44 inches, such as 0.4 inches.

The diameter 583 of the valve stem 506 between the seating members 510 may be between 0.22 and 0.33 inches, such as 0.275 inches with a tolerance of +/−0.003 inches.

The length 582 of the valve stem 506 from the distal end 555 to the proximal end 545 may be between 1.5 and 2 inches, such as 1.793 inches. The diameter of orifice 530-1 may be between 0.125 and 0.165 inches, such as 0.151 inches with a tolerance of +/−0.003 inches. Referring to the cross-section 540, the outer width 586 of orifice 530-3 may be between 0.026 and 0.226, such as 0.126 inches. The angle 588 between the internal walls of lumen 528 and/or orifice 530-3 may be between 0 and 10 degrees, such as 2 degrees.

Figure 6B:
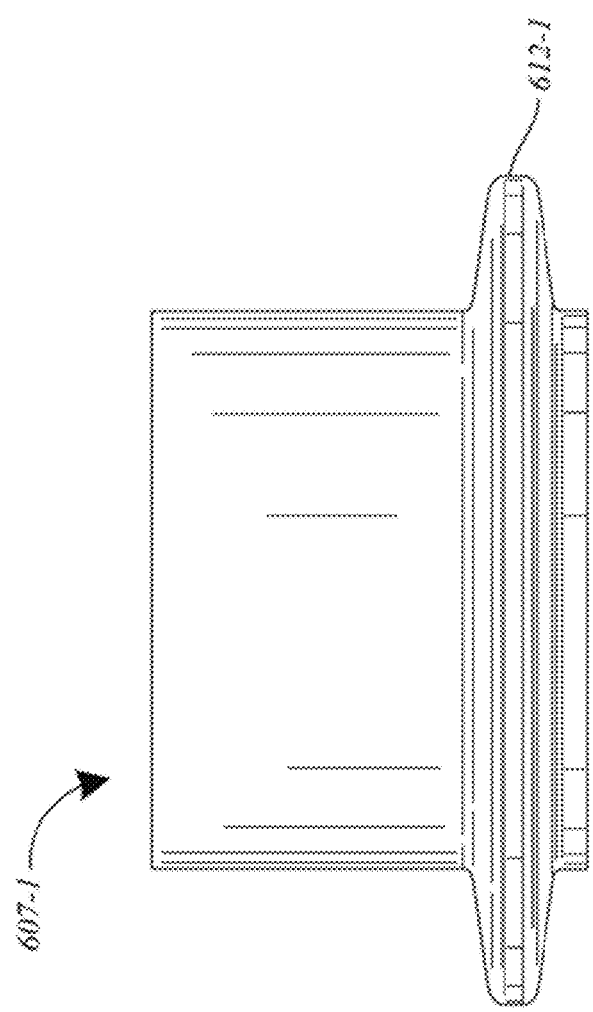
Figure 6D:
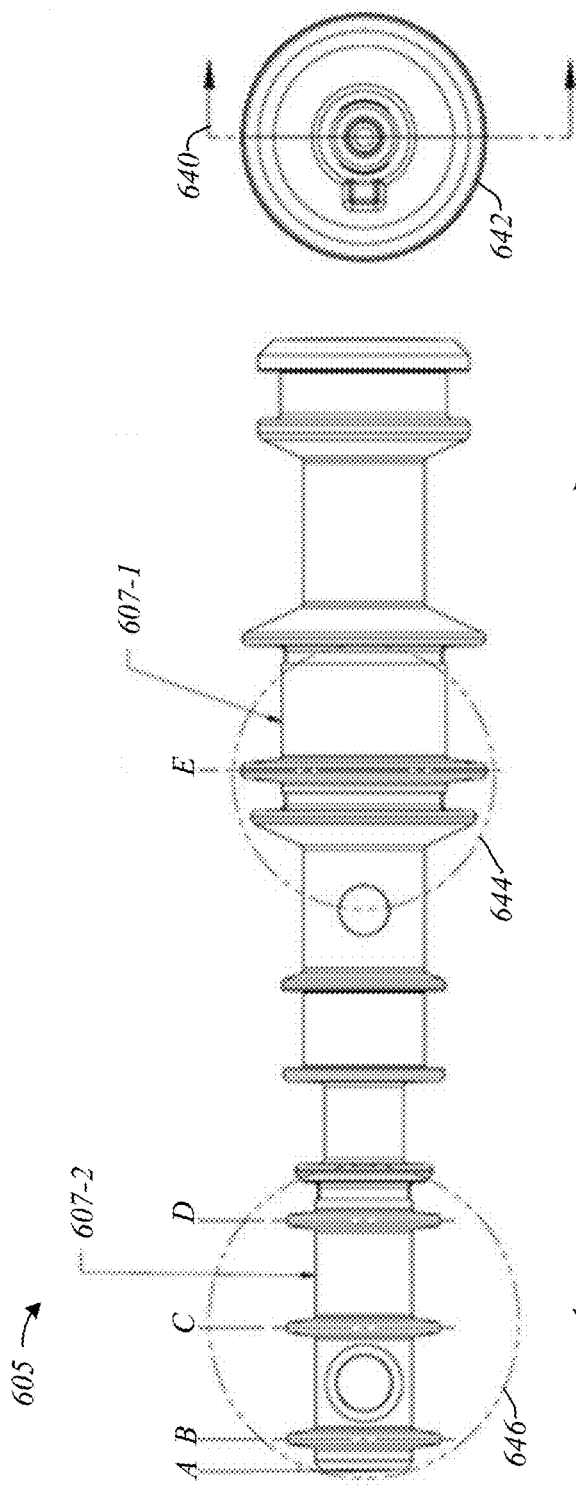
Figure 6E:
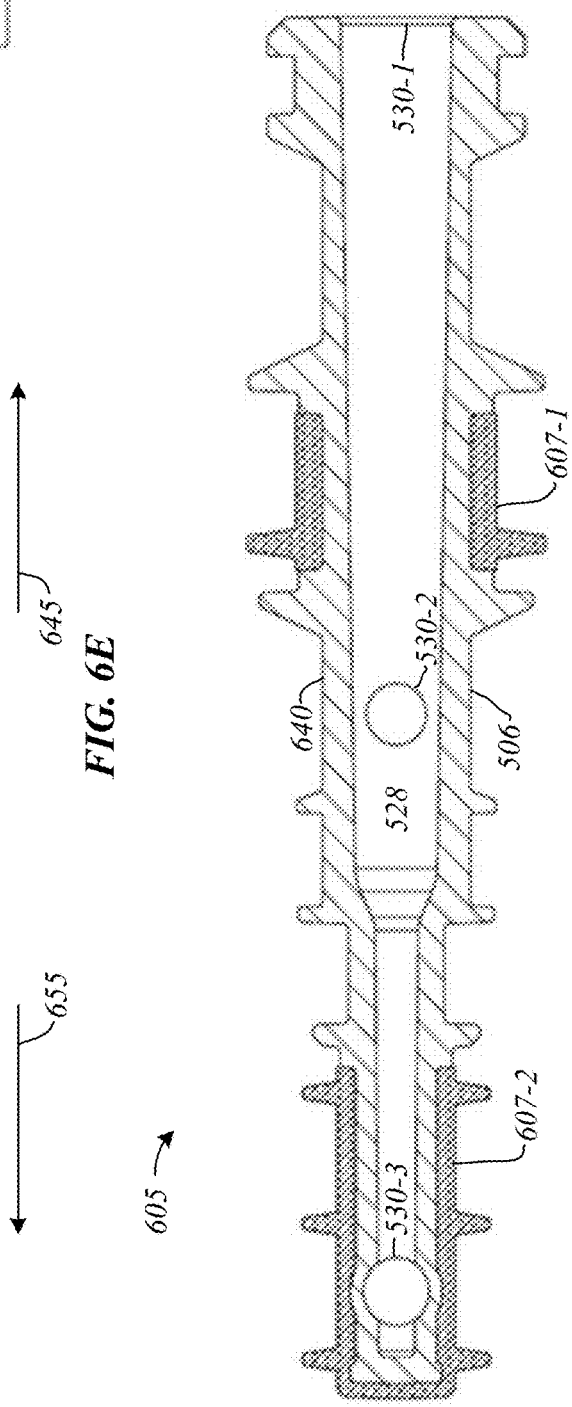
Figure 6F:
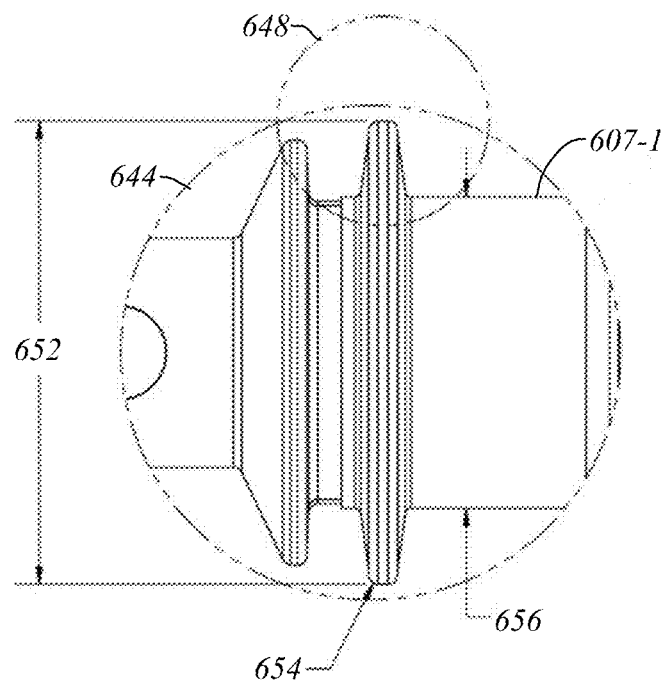
Figure 6G:
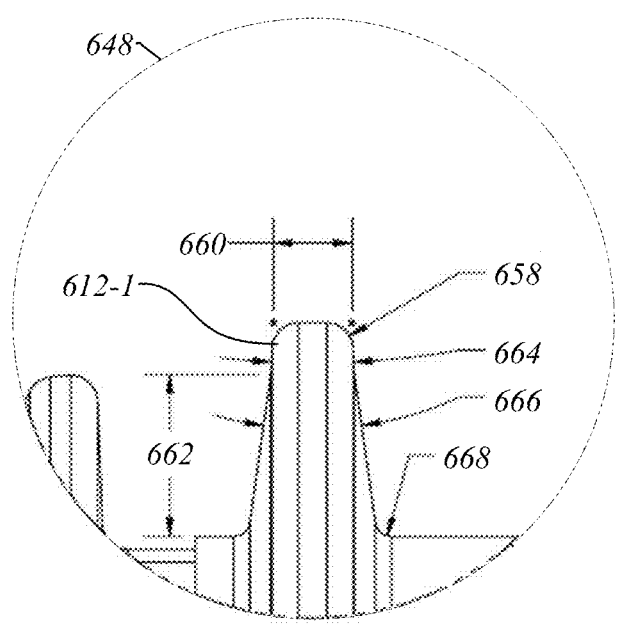
Figure 6H:
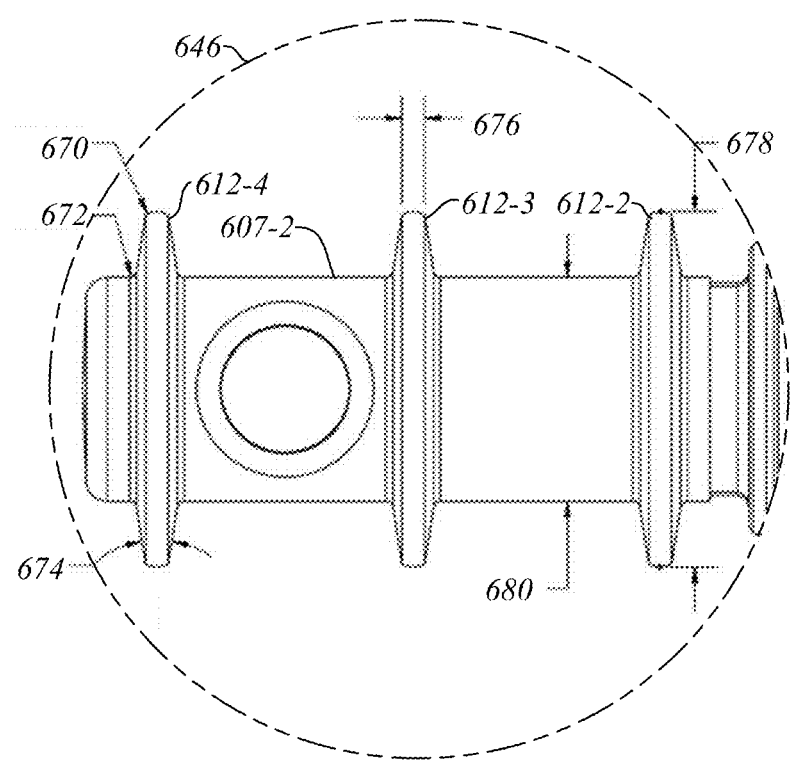

FIGS. 6A-6H illustrate various aspects of an exemplary valve stem assembly 605 according to the present disclosure described herein. FIG. 6A illustrates a perspective view of the valve stem assembly 605. The valve stem assembly 605 may include a proximal end 645, a distal end 655, seal assemblies 607-1, 607-2. Seal assembly 607-1 may include seal 612-1 and seal assembly 607-2 may include seals 612-2, 612-3, 612-4. In one or more embodiments described herein, seal assemblies 607 may be overmolded onto valve stem 506. FIGS. 6B and 6C illustrate seal assembly 607-1 and seal assembly 607-2 with opening 631, respectively. FIG. 6D illustrates a first side view of the valve stem assembly 605 and a top view of the proximal end of the valve stem assembly 605. FIG. 6E illustrates a cross-section 540 of valve stem assembly 605. FIG. 6F illustrates a detail of seal assembly 607-1 and FIG. 6G illustrates a detail of seal 612-1 of seal assembly 607-1. FIG. 6H illustrates a detail of seal assembly 607-2. In many embodiments, one or more components illustrated in FIGS. 6A-6H may be the same or similar in construction, function, and/or appearance as one or more other components described herein. For example, one-way valve 108 may be used with valve stem assembly 605, such as between retaining flanges 516-1, 516-2. Embodiments are not limited in this context.

Referring to FIG. 6B, in one or more embodiments, seal assembly 607-1 may be overmolded onto valve stem 506 between retaining flanges 516-4, 516-6. Referring to FIG. 6C, in one or more embodiments, seal assembly 607-2 may be overmolded onto valve stem 506 about the distal end 555 and up to the distal side of retaining flange 516-5. In the illustrated embodiment, seal assembly 607-2 includes opening 631. Opening 631 may facilitate fluid to flow into and out of the lumen 528 via orifice 530-3. In some embodiments, opening 631 may be referred to as a window. As previously mentioned, a lip surrounds orifice 530-3. In many embodiments, the lip surrounding orifice 530-3 may cause opening 631 to form during an overmolding procedure to form seal assembly 607-2. Further, the lip may prevent flow from the overmolding procedure from entering the lumen 528 via orifice 530-3.

In some embodiments, the construction of the seals of seal assemblies 607 being molded plastic, rather than O-rings, may allow them to be molded with a thickness that is less than an O-ring. As such, such molded seals may be designed with a diameter that is greater than an O-ring. Given that the molded seals may thinner and/or of greater diameter than O-ring seals, may provide performance benefits to the valves, compared to valves with O-ring seals. For example, molded seals with greater diameter, but having a flexibility which allows them to slide in a valve well, may provide more surface area contact and sealing against the valve well wall.

FIG. 6D illustrates a side view of valve stem assembly 605 with proximal and distal ends 645, 655 and a front view 642 of the proximal end 645 of valve stem assembly 605. In FIG. 6D, the side view of valve stem assembly 605 includes seal assemblies 607 and details 644, 646 are identified (see FIGS. 6F and 6H). In the front view 642 of the proximal end 645, cross-section 640 is identified. Additionally, FIG. 6D may include reference points A-E. Reference point A may be the distal end 555 of the valve stem assembly 605. Reference point B may be at seal 612-4 and the distance between reference points A and B may be between 0.043 and 0.063 inches, such as 0.053 inches. Reference point C may be at seal 612-3 and the distance between reference points A and C may be between 0.13 and 0.33 inches, such as 0.234 inches. Reference point D may be at seal 612-2 and the distance between reference points A and D may be between 0.30 and 0.50 inches, such as 0.409 inches. Reference point E may be at seal 612-1 and the distance between reference points A and E may be between 1.04 and 1.24 inches, such as 1.144 inches.

In FIG. 6E, the cross-section 640 of valve stem assembly 605 is illustrated with valve stem 506 and seal assemblies 607. The valve stem 506 includes lumen 528 and orifices 530. As shown, seal assembly 607-1 may be formed between retaining flanges 516-4, 516-6 and seal assembly 607-1 may be formed to encapsulate the distal end 555 of the valve stem 506 and extend up to retaining flange 516-5. In one or more embodiments, valve stem assembly 605 may include a one-way seal positioned between retaining flanges 516-1, 516-2 (see e.g., one-way seal 108 in FIGS. 1A and 1B. In some embodiments, the one-way seal may be overmolded. In other embodiments, the one-way seal may be loaded onto the valve stem 506, such as after overmolding one or more of seal assemblies 607.

FIG. 6F illustrates detail 644 of seal assembly 607-1. In the detail 644 of seal assembly 607-1 detail 648 of seal 612-1 is identified (see FIG. 6G). As illustrated in FIG. 6F, seal 612-1 may have an outer diameter of between 0.35 and 0.45 inches, such as 0.404 inches. In many embodiments, outer diameter of seal 612-1 may have a radius 654 on the proximal and/or distal sides. In several embodiments, the rounding radius 654 is between 0.001 and 0.018 inches, such as 0.008 inches. The outer diameter 656 of seal assembly 607-1 may be between 0.23 inches and 0.31 inches, such as 0.272 inches. For example, the outer diameter of seal assembly 607-1 may be 0.27 inches on both sides of seal 512-1.

Referring to detail 648 of FIG. 6G, seal 612-1 may include a width 660 of between 0.14 and 0.34 inches, such as 0.24 inches with a positive tolerance of 0.003 inches and a negative tolerance of 0.001 inches. In many embodiments, the proximal and distal edges of seal 612-1 may have a radius 654. In several embodiments, the radius 654 is between 0.001 and 0.018 inches, such as 0.008 inches. The angles 664, 666 may be slopes in the radial direction of the proximal and distal sides of seal 612-1. For example, seal 612-1 may converge in the radial direction proximate the radial extent of the seal at an angle 664 between 3 and 10 degrees, such as 5.5 degrees. Additionally, or alternatively, seal 612-1 may converge in the radial direction proximate the valve stem 506 at an angle 666 between 9 and 23 degrees, such as 16 degrees. In many embodiment, the portion of seal 612-1 with an angle 666 may transition to the portion of seal 612-1 with angle 664 around 0.05 inches from outer diameter 656.

FIG. 6H illustrates detail 646 of seal assembly 607-2 with seals 612-2, 612-3, 612-4. As illustrated in FIG. 6H, seals 612-2, 612-3, 612-4 may each have an outer diameter between 0.19 and 0.31 inches, such as 0.254 inches. Each of the seals 612-2, 612-3, 612-4 may include a width 676 of between 0.06 and 0.26 inches, such as 0.16 inches with a positive tolerance of 0.003 inches and a negative tolerance of 0.001 inches. In many embodiments, the proximal and distal edges of each of the seals 612-2, 612-3, 612-4 may have a radius 670. In several embodiments, the radius 654 is between 0.006 and 0.026 inches, such as 0.016 inches. The angle 674 may be between the slopes in the radial direction of the proximal and distal sides of each of seals 612-2, 612-3, 612-4. For example, each of seals 612-2, 612-3, 612-4 may converge in the radial direction at an angle 674 between 13 and 22 degrees, such as 17.9 degrees. In many embodiments, the seal assembly 607-2 may have an outer diameter 680 of between 0.06 and 0.26 inches, such as 0.16 inches, on the flat portions that are both proximal and distal to one or more of the seals 612-2, 612-3, 612-4. Further, the proximal and distal sides of the seals 612-2, 612-3, 612-4 may have a radius of between 0.001 and 0.015 inches, such as 0.005 inches, at transitions to and/or from the outer diameter 680.

The dimensions and/or composition of one or more components of valve stem assembly 605 may facilitate one or more functionalities of the seals. In various embodiments, the sealing function of the seals may be adjusted by varying dimensions and/or composition of the valve stem assembly. In many embodiments, the combination of a relatively thick base with a relatively thin outer rim allows the seal to function in a pressurized system. For example, the thin outer rim of the seals can provide the required flexibility while the transition to the thicker base closer to the outside diameter of the stem resists deformation. This may be done in order to maintain the appropriate radially opposing force at the end of the seals to maintain contact with the wall of the valve well even when the contents (e.g., fluid) it is sealing against becomes pressurized.

As previously mentioned, in various embodiments, the valve stem 506 may include one or more monolithic aspects. For example, retaining flanges 516 may be integrally formed with valve stem 506. Further, an interface member may also function to seal an orifice in a valve stem. In some such embodiments, a lumen may be left when a core forming pin is removed via the orifice. Accordingly, one or more components described herein can eliminate processing steps, the number of materials used, as well as assembly complexity, thus reducing cost of the overall cleaning valve. In several embodiments, a core pin may be used to create the lumen of the valve stem 506. Further, the core pin may be used to manipulate (e.g., position and reposition) the valve stem 506 during formation. The lumen may fluidly connect the orifices to allow for fluid (e.g., liquid or gas) flow through the lumen of the valve stem. However, the core pin may leave an orifice (e.g., orifice 530-1) in the valve stem for removal of the core pin (e.g., in the proximal end) that needs to be plugged to constrain fluid flow between the radial orifices (e.g., orifices 530-2, 530-3) of the stem. In various embodiments, this orifice may be plugged via the interface member (e.g., stem plug 122, 422), which may be formed of silicone, thermoplastic elastomer (TPE), or some other flexible material that can be used to form an interference snap fit over the proximal end of the stem.

A cap, such as one with conformable material and an interference fit (e.g., interface member 104, 404), can act as a seal at the proximal end of the valve stem assembly 605 once assembled thereon (e.g., via stem plug 422). This seal may prevent leaks at the proximal end of the stem during use. Some alternative methods of sealing with alternative components could include press fitting a plug of the same material as the stem into the end of the stem. In various embodiments, the plug could remain in place due to the press fit, or it could be ultrasonically welded, glued or any other fastening method.

In some embodiments, the one-way seal can be loaded over the monolithic stem and fit into the receiving well on the stem of a snap fit or the one-way seal could be over-molded (e.g., from silicone, TPE, or some other flexible material) directly onto the stem as a secondary process. In various embodiments, one or more of the seals 612 may be formed/assembled in the same or similar manner. In some embodiments, one or more surface treatments may be applied to the valve stem 506. For example, one or more surface treatments may be used to clean and/or lubricate the valve stem 506, such as prior to an overmolding procedure. In various embodiments, one or more components may be plugged and/or masked prior to surface treatments. For instance, the orifices 530 may be plugged prior to a lubricating surface treatment.

All dimensions are illustrative only, and other dimensions may be more suited to a particular application. Also, dimensions described may be approximations that encompass tolerances, e.g., tolerances allow for plus or minus variations from the described values (e.g., +/− a percentage, +/− a length, and/or +/− an angle). Although many dimensions are discussed in terms of inches, inches can readily be converted to millimeters (mm) based on 1 inch equaling 25.4 mm. Unless otherwise noted, tolerances may be as follows: "X" is ±0.25 mm; "X.X" is ±0.1 inches or ±0.1 mm; "X.XX" is ±0.01 inches or ±0.05 mm; "X.XXX" is ±0.05 inches or ±0.01 mm; "X.XXXX" is ±0.0005 inches; and angles may be ±2 degrees. In various embodiments, FIGS. 5B, 5C, 6D-6E may be interpreted in accordance with American Society of Mechanical Engineers Y14.5M-2009 standard. In various embodiments, the valve stem 506 may be formed from a polycarbonate and the seal assemblies 607 may be formed from a thermoplastic elastomer. For example, the valve stem 506 may be formed in a first shot of polycarbonate and the seal assemblies 607 may be formed in a second shot of thermoplastic elastomer.

FIGS. 7A-7G illustrate exemplary indicators for cleaning valve assemblies (or cleaning valves) according to the present disclosure described herein. One or more of the cleaning valves disclosed herein may include features and/or components to facilitate differentiation from procedural valves (i.e., valves for use in a procedure performed on a patient). Further, the features and/or components described herein may be used in any combination to facilitate differentiation from procedural valves. For example, the feel and/or look may be varied from a procedural valve, including a differentiation in shape, color, material, and other visual and/or tactile indicators. In another example, an additional component, such as an indicator, may be included to facilitate differentiation from procedural valves. Embodiments are not limited in this context.

Figure 7A:
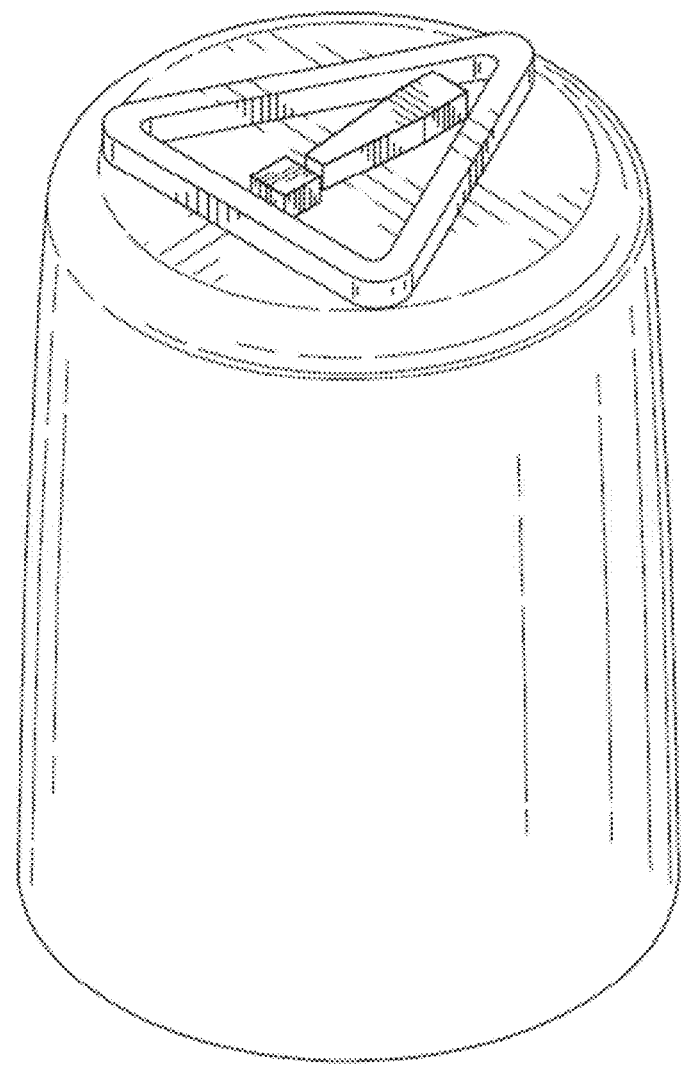
FIGS. 7A-7G illustrate exemplary indicators according to the present disclosure described herein.
Figure 7B:
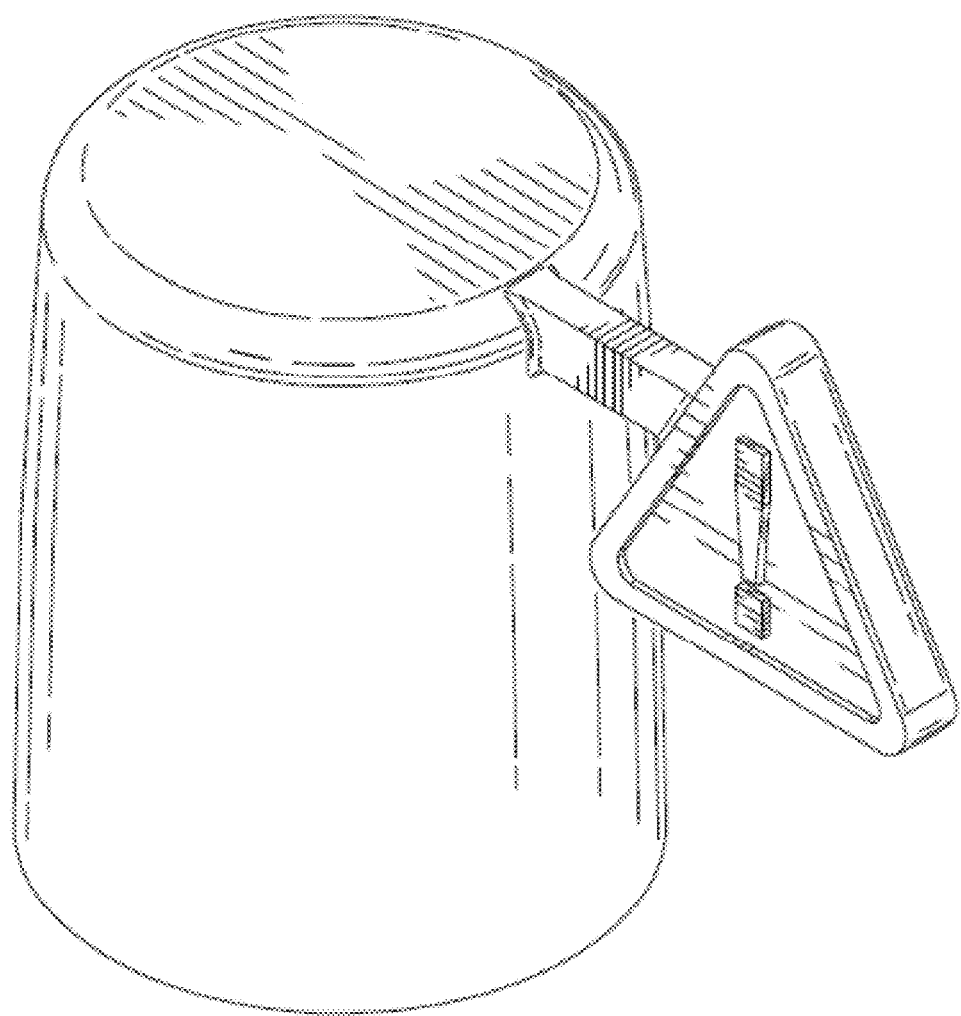
Figure 7C:
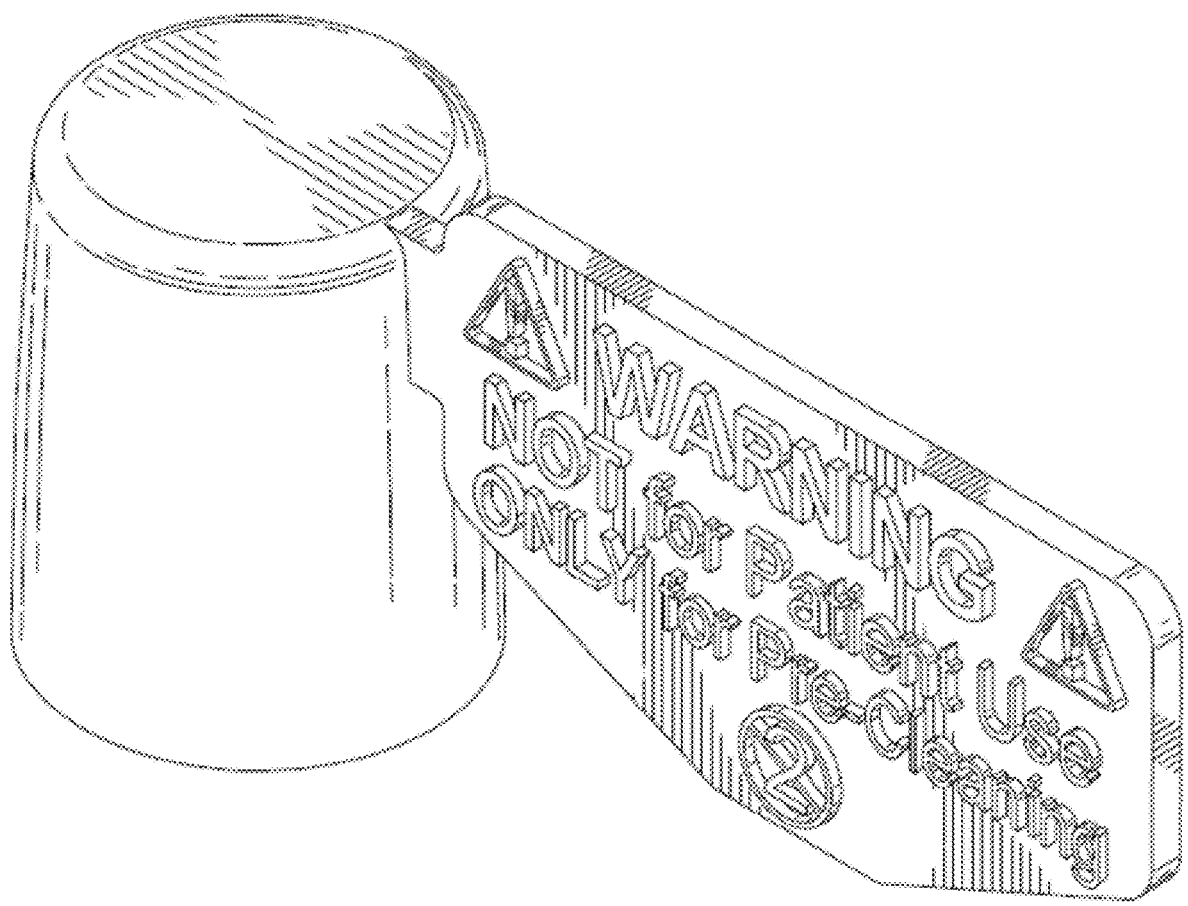
Figure 7D:
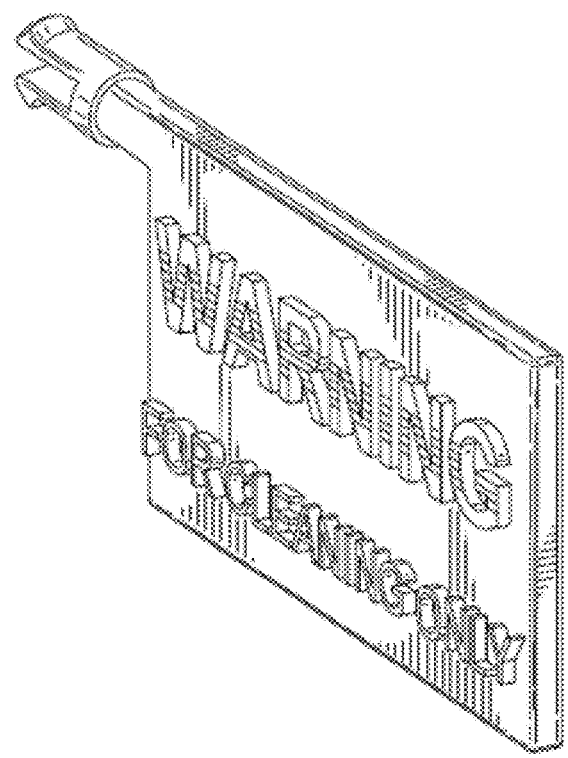
Figure 7E:
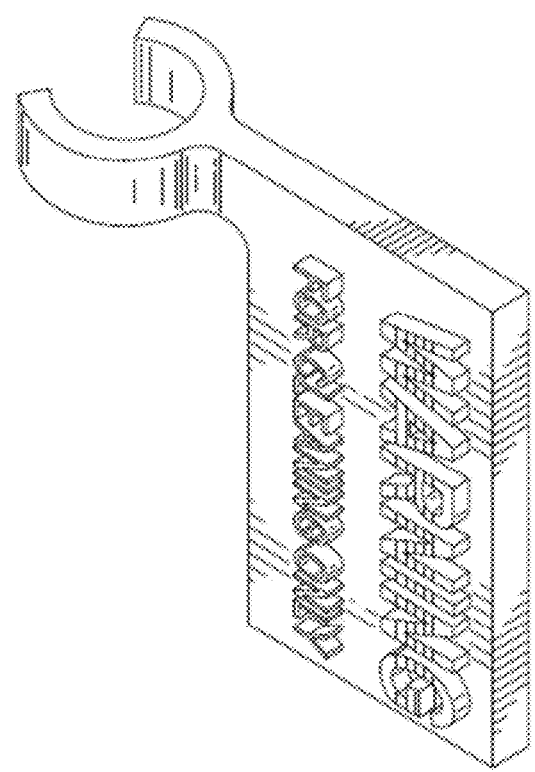
Figure 7F:
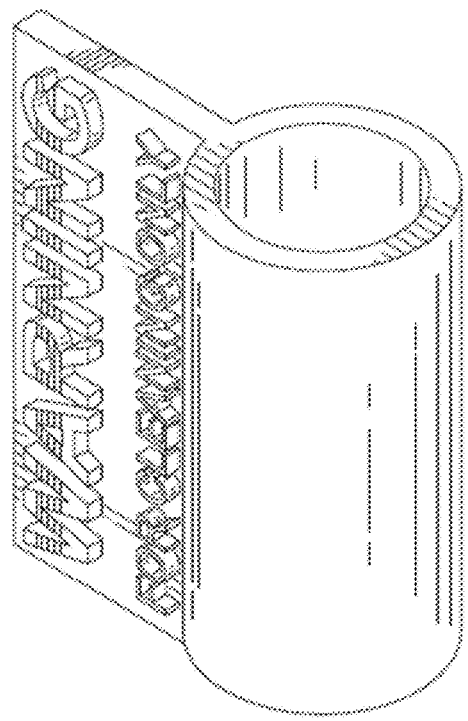
Figure 7G:
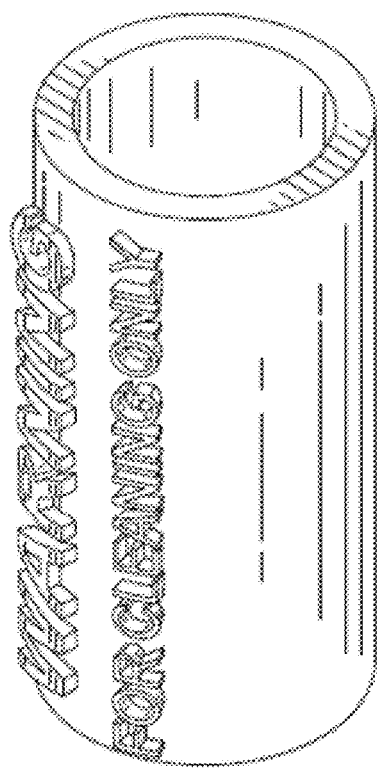

In several embodiments, an indicator (e.g., warning) of some kind may be included in or on the valve. For example, ways of including a warning on the valve for differentiating a cleaning valve from a procedural valve could include pad printing or laser etching a warning directly onto the user interface (e.g., spring cap or button) or exposed surface of the cleaning valve during use. In many embodiments, indicators described herein may include one or more raised surfaces with various features (e.g., texture, color, etc.) configured to differentiate a cleaning valve from a procedural valve. Alternatively, or additionally, a warning label could be embossed on the side of the user interface (e.g., spring cap or button), providing a warning that protrudes out from the side of the valve and is felt and clearly visible during use. This could be located on the side of the valve, or on the top surface forcing the user to feel the warning when they depress the valve. An example of this can be seen in FIG. 7A. Alternatively, or additionally, a warning tag could be molded into the cap and integrally attached as part of the component as seen in FIGS. 7B and 7C. As will be appreciated, the text and/or symbols may be varied (as long as they facilitate differentiation from a procedural valve) without departing from the scope of this disclosure.

In many embodiments, there may be an additional component that slides over or removably attaches to the seal end of the valve stem in the packaging with a shape that prevents the valve from being inserted into the valve well of the endoscope without the additional component first being removed. See e.g., FIGS. 7D-7G. In many embodiments, a portion of this component may be inserted through a radial hole, orifice, or aperture of the valve stem. See e.g., FIG. 7D. In various embodiments, this component may clip to the valve stem. See e.g., FIG. 7E. In some embodiments, this component could be hollow with an inside diameter large enough to slide over the end of the valve stem and an outside diameter large enough such that it has an interference fit with the valve well on the scope so it is unable to be inserted. See e.g., FIGS. 7F and 7G. Other cleaning valve assembly related techniques, features, and/or components that may be used herein are disclosed in U.S. Non-Provisional Patent Application titled "Devices, Systems, and Methods for Medical Cleaning Valves and Indicators", filed even date herewith, the entirety of which is incorporated herein by reference.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure.

What is claimed is:

1. A valve for a medical device, comprising:
    a valve stem including a proximal end, a distal end, one or more orifices, and a lumen in fluid communication with at least one orifice in the one or more orifices, wherein the proximal end of the valve stem comprises a first orifice of the one or more orifices;
    one or more seals positioned between the proximal and distal ends of the valve stem; and
    an interface member configured to seal the first orifice of the one or more orifices when the valve stem is coupled with the interface member, wherein the interface member is configured to surround a first seal of the one or more seals when the valve stem is coupled with the interface member.

2. The valve of claim 1, wherein the valve stem and the one or more seals are formed from a polymer.

3. The valve of claim 1, wherein the one or more orifices comprise the first orifice and a second orifices positioned between the proximal and distal ends of the valve stem.

4. The valve of claim 3, wherein the one or more seals comprise the first seal and a second seals positioned between the first and second orifices.

5. The valve of claim 4, wherein the one or more seals comprise a third seal positioned distal of the first and second orifices.

6. The valve of claim 1, wherein the one or more seals includes a seal with a first portion having a first thickness and a second portion having second thickness thinner than the first thickness.

7. The valve of claim 6, wherein the first thickness is greater than 0.015 inches and the second thickness is less than 0.015 inches.

8. The valve of claim 6, wherein the first thickness of the seal transitions into the second thickness of the seal at an angle between 25 and 45 degrees.

9. The valve of claim 6, wherein the second portion extends at least 0.01 inches radially outward beyond the first portion.

10. The valve of claim 9, wherein the second portion is configured to form an interference fit with a valve well.

11. The valve of claim 1, wherein the valve stem comprises a monolithic stem integrally formed with at least one of the one or more seals.

12. A method of manufacture, comprising: forming, as a unitary structure, a valve stem including a proximal end, a distal end, one or more seals positioned between the proximal and distal ends of the valve stem, one or more orifices, and a lumen in fluid communication with at least one orifice of the one or more orifices, wherein the proximal end of the valve stem comprises a first orifice of the one or more orifices; and sealing the first orifice by coupling an interface member to the valve stem, wherein the interface member is configured to surround a first seal of the one or more seals when the valve stem is coupled with the interface member.

13. The method of claim 12, comprising removing a forming core pin from the lumen via an orifice of the one or more orifices, wherein the orifice is comprised in the proximal end of the valve stem.

14. The method of claim 12, comprising forming the valve stem with a closed distal end.

15. The method of claim 12, comprising forming at least one seal in the one or more seals with a first portion having a first thickness and a second portion having a second thickness, wherein the second portion is radially outward of the first portion and the second thickness is thinner than the first thickness.

16. The method of claim 12, wherein the valve stem comprises a monolithic stem integrally formed with at least one of the one or more seals.

17. A valve for a medical device, comprising:
    an interface member;
    a valve stem to which the interface member is removably couplable, the valve stem including a proximal end, a distal end, two or more orifices, and a lumen in fluid communication with first and second orifices of the two or more orifices, wherein the first orifice is located proximate the distal end of the valve stem, and wherein the lumen is plugged at the proximal end of the valve stem by the interface member; and
    two or more seals, wherein a first seal of the two or more seals is positioned between the proximal end of the valve stem and the second orifice, and a second seal of the two or more seals is positioned between the second orifice and the distal end of the valve stem,
    wherein the interface member is configured to surround the first seal when the interface member is coupled to the valve.

18. The valve of claim 17, wherein the distal end of the valve stem is closed and the lumen terminates at or distally beyond the first orifice and before the closed distal end.

19. The valve of claim 17, wherein the valve stem comprises a monolithic stem integrally formed with at least one of the two or more seals.

* * * * *